(12) United States Patent
Caratsch

(10) Patent No.: US 11,234,834 B2
(45) Date of Patent: Feb. 1, 2022

(54) INTERBODY CAGE AND METHOD OF INSERTION

(71) Applicant: Twist Technologies Sàrl, Trelex (CH)

(72) Inventor: Alexandre Caratsch, Trelex (CH)

(73) Assignee: TWIST TECHNOLOGIES SÀRL, Trélex (CH)

( * ) Notice: Subject to any disclaimer, the term of this patent is extended or adjusted under 35 U.S.C. 154(b) by 1018 days.

(21) Appl. No.: 15/739,696

(22) PCT Filed: Jun. 22, 2016

(86) PCT No.: PCT/IB2016/053693
§ 371 (c)(1),
(2) Date: Jun. 6, 2018

(87) PCT Pub. No.: WO2016/207798
PCT Pub. Date: Dec. 29, 2016

(65) Prior Publication Data
US 2021/0196469 A1 Jul. 1, 2021

(30) Foreign Application Priority Data

Jun. 25, 2015 (EP) .................................... 15173883
Jun. 25, 2015 (EP) .................................... 15173887
Sep. 1, 2015 (EP) .................................... 15183289

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4425* (2013.01); *A61F 2/4611* (2013.01); *A61F 2002/30148* (2013.01); *A61F 2002/443* (2013.01)

(58) Field of Classification Search
CPC ...... A61F 2/447; A61F 2/4425; A61F 2/4611; A61F 2/4455; A61F 2/4603; A61F 2250/0006; A61F 2230/0091; A61F 2002/30148; A61F 2002/443; A61F 2002/30593; A61F 2002/3082; A61F 2002/30841; A61F 2002/30785;
(Continued)

(56) References Cited

U.S. PATENT DOCUMENTS 9,289,314 B2 * 3/2016 Perisic .................. A61F 2/4455
2013/0150969 A1 * 6/2013 Zipnick .......... A61B 17/320016
623/17.16

* cited by examiner

*Primary Examiner* — Pedro Philogene
(74) *Attorney, Agent, or Firm* — Pavé Law Group, LLC; Raj S. Davé

(57) ABSTRACT

An interbody cage which comprises a cage body and a mobile rotational element which, when said mobile element is rotated around a longitudinal axis of the body of the cage, may engage one or both adjoining vertebrae and temporally distract the intervertebral space for easier insertion of the cage body. The rotational element may also be designed to durably engage the adjoining vertebrae after its rotation, so as to allow a durable increase of the distraction of the vertebrae. Methods of insertion of the interbody cage are provided wherein the vertebrae are first distracted by the insertion of the cage or of the mobile element, then further distracted by rotation of the mobile element, before the cage is fully inserted into the intervertebral space without the body's superior and inferior surfaces fully engaging the vertebrae in the process.

19 Claims, 24 Drawing Sheets

(58) Field of Classification Search
CPC .... A61F 2002/30289; A61F 2002/2835; A61F 2002/4623; A61B 17/025
USPC .......................................... 623/17.11–17.16
See application file for complete search history.

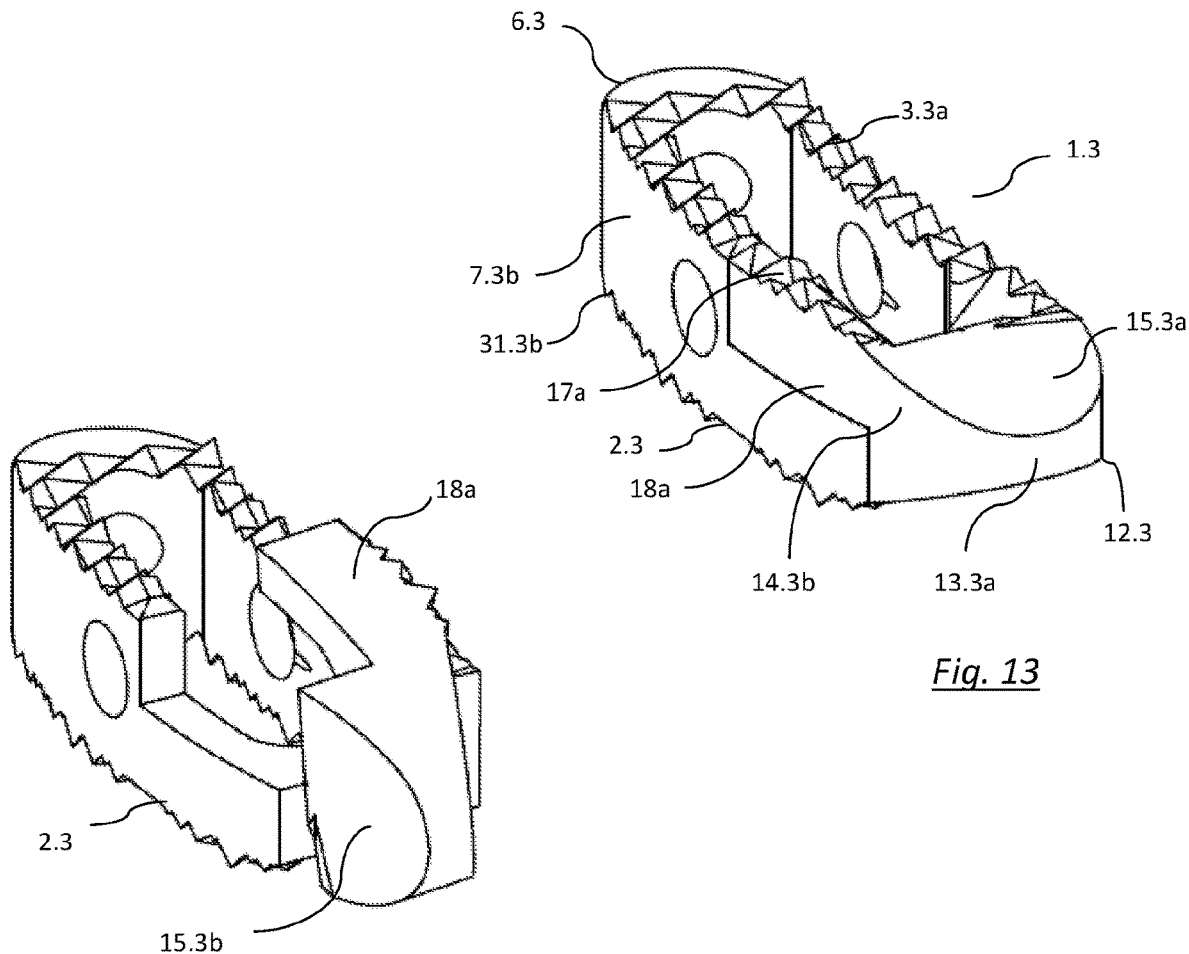
Fig. 14a
Fig. 13
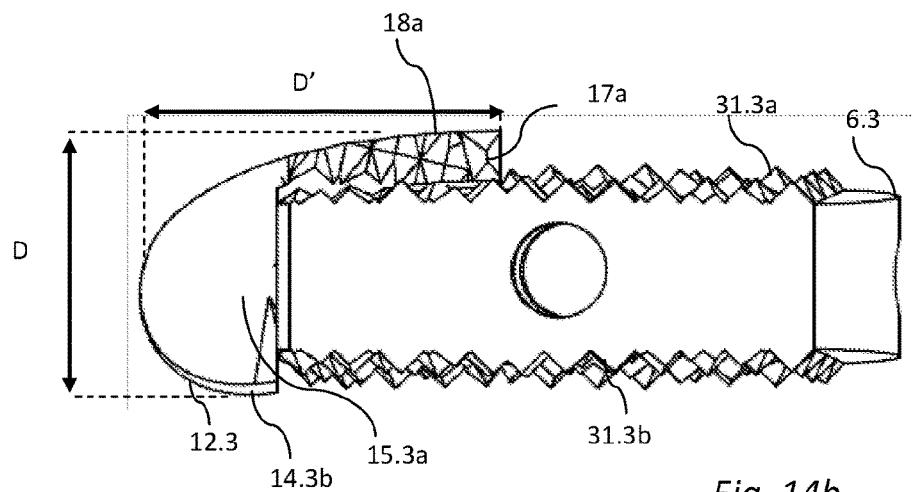
Fig. 14b

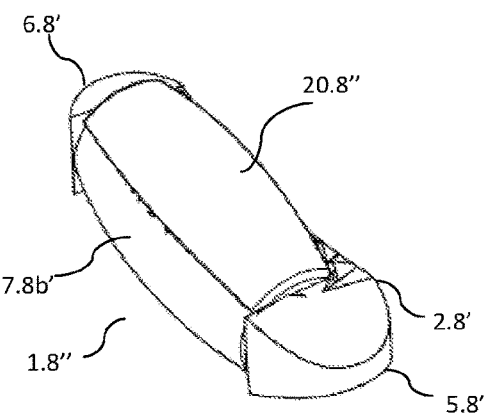
*Fig. 26a*
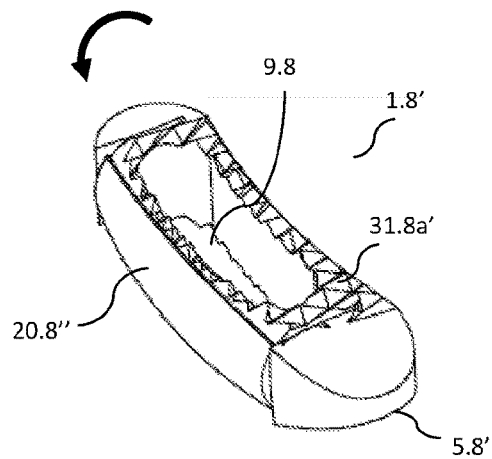
*Fig. 26b*
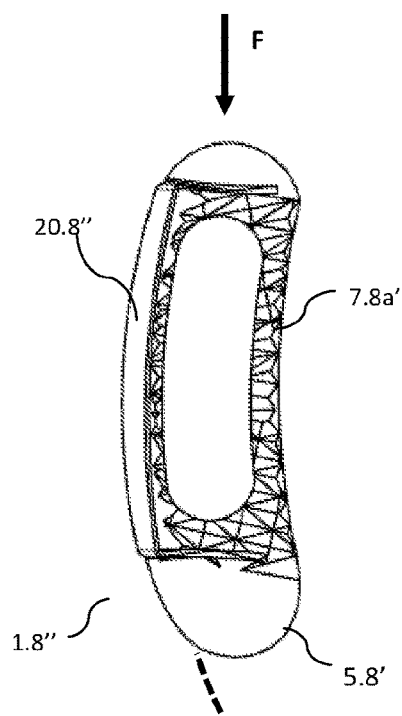
*Fig. 26c*
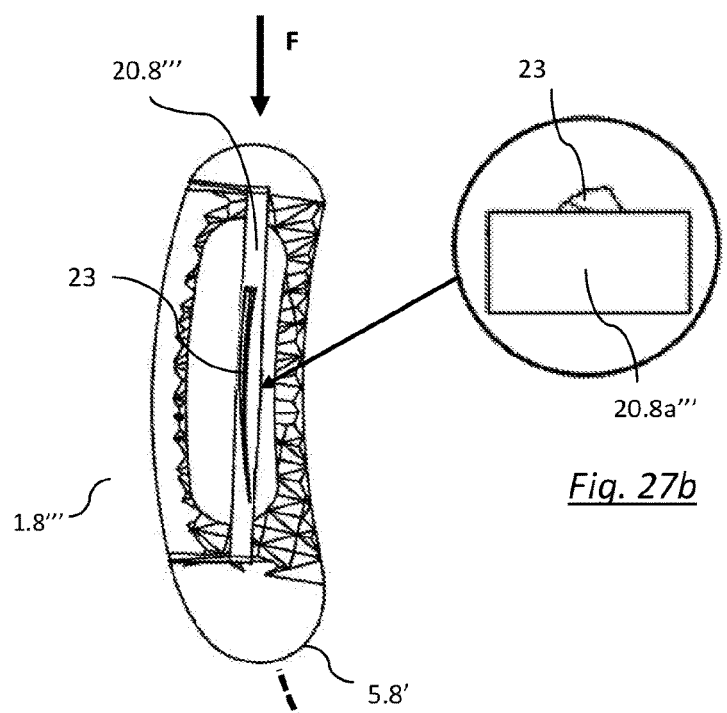
*Fig. 27a*
*Fig. 27b*

INTERBODY CAGE AND METHOD OF INSERTION

CROSS-REFERENCE TO RELATED APPLICATIONS

This application is the U.S. national stage application to International Patent Application No. PCT/IB2016/053693, filed Jun. 22, 2016, which claims the benefit of foreign priority to European Patent Application Nos. 15183289.6, filed Sep. 1, 2015, 15173883.8, filed Jun. 25, 2015 and 1517388739, filed Jun. 25, 2015, the contents of which are incorporated herein by reference in their entireties.

The present invention relates to the medical field, and more particularly to an interbody cage with a mobile rotational element and a method of insertion of said interbody cage.

Certain pathologies of the human spine, such as degenerated discs, facettes diseases, and dislocation of vertebrae, compromise the support capacity of the column and the sharing of the load.

The treatment of such pathologies in their advanced stages is achieved by various stabilization systems with intra-discal implants such as interbody cages, whether or not coupled with extra-discal systems, which combine the use of vertebral screws and plates or rods. Such intra-discal implants have significantly improved the treatment of pathologies of the human spine, in restoring the intervertebral space, which results in the decompression of the nerve roots and the acceleration of bony fusion of the adjacent vertebrae together.

Impactation cages represent an important category among interbody cages. These cages, which have a substantially parallelepiped shape, are inserted between the vertebrae by impactation. The downside of these cages is the difficulty of their insertion into the intervertebral space, in particular through posterior or unilateral approaches, notably transforaminal, lateral, oblique or anterio lateral, but also for anterior cages. The dents and crenellations which are integrated on the superior and inferior surfaces of the cage for the purpose of anchoring the cage into the vertebral plates to prevent its migration, once it is in its final position, represent an additional obstacle to its insertion.

US2002029082 discloses an interbody implant comprising one first component serving as spacer between two vertebrae which is inserted in the interbody in a first configuration and is then rotated in a second and final configuration to distract the two vertebrae and maintain them distracted, and one second component, coupled to the first component's posterior side, which is serving as stabilizer of the first component in its second position, the whole implant representing a T shape when viewed from above.

US 2008/0269758 discloses an assembly comprising of a U-shaped distractor component used to distract adjoining vertebrae by a 90° rotation and a elliptical bone tray which is slid into the interbody space to stabilize the distractor component.

U.S. Pat. No. 9,289,314 discloses an interbody cage comprising a cage body and mobile flaps which may be rotated around the longitudinal axis of the cage body to serve as means of distraction of the interbody space to facilitate the insertion of the cage.

US2012/0109319 discloses an interbody cage comprising one cage body and one mobile flattened rectangular shaped insertion tip, wherein the insertion tip is first introduced between two vertebrae in one position and thereafter rotated 90° along the longitudinal axis of the cage body so as to expand the interbody space in order to thereafter introduce the cage body. After the insertion of the cage between the vertebrae, the insertion tip is rotated again and pulled back within a slit in the cage body, thus allowing for a distraction of the anterior portion of the cage body and the increase of its angulation relative to the posterior side of the cage.

U.S. Pat. No. 8,641,765 discloses an interbody cage comprising one first implant spacer body and one second implant spacer body, wherein the second implant spacer body are able to rotate relative to each other and wherein the second implant spacer body has a minor axis and a major axis. As is US2012/0109319, the major axis of the second spacer body is used to expand the vertebrae by rotation of approximately 90°.

The purpose of the present invention is to provide an interbody cage which comprises a cage body and a mobile rotational element which, when said mobile component is rotated around a longitudinal axis of the body of the cage, may engage one or both adjoining vertebrae and temporally distract the intervertebral space for easier insertion of the cage body. The deployment of the mobile rotational element through rotation and its durable engagement with the adjoining vertebrae may also allow a durable increase of the distraction of the vertebrae. Methods of insertion of the interbody cage are provided wherein the vertebrae are first distracted by the insertion of the anterior side of the cage, then further distracted by rotation of the mobile rotational element, before the cage is fully inserted into the intervertebral space without the body's superior and inferior surfaces fully engaging the vertebrae in the process, and after a final step of counter-rotation or a further rotation of the rotational element, a large portion of the superior and inferior surface of the body, and in certain embodiments a portion of the rotational element, may engage the adjoining vertebrae.

The characteristics of the invention will appear more clearly from the description of various embodiments, which are solely provided as examples and are not limitative, and in which references will notably be made to the anterior side of the cage or body thus defining that side which is adjusted against the vertebral bodies just before the introduction of said cage or body into the interbody space, and to the posterior side of the cage body which shall define the side opposite to the anterior side. The description of these various embodiments refers to the attached schematic Figures in which:

FIG. 13 represents a perspective view of the crescent-shaped interbody cage according to the fourth embodiment with a non-deployed rotational element.

FIG. 14a represents the same perspective view of the cage of the fourth embodiment as in FIG. 1 but with a fully deployed rotational element.

FIG. 14b represents a lateral view of the same cage represented in FIG. 14a with fully deployed rotational element.

FIG. 16b represents a front view of the interbody cage of FIG. 16a.

FIG. 18b represents a lateral view of the interbody cage in the configuration of FIG. 18a.

FIG. 22b represents a front view of the cage in the configuration of FIG. 22a.

FIG. 26a represents a perspective view of another variation of the ninth embodiment with a crescent-shaped caged and fully deployed rotund shield.

FIG. 26b represents a perspective view of the same crescent-shaped cage as in FIG. 26a, but with a fully collapsed rotund shield.

FIG. 26c represents a top down view of the crescent shaped cage in the same configuration as in FIG. 26b with collapsed rotund shield.

FIG. 27a represents a top down view of a variation of the crescent shaped cage of FIG. 25b with a deployed single arc comprising a curved ridge on its outward facing side.

FIG. 27b represents in a blown-up front view of a detail of a section of the arc with the ridge of the cage in FIG. 27a.

FIG. 31b represents a front view of the cage in the same configuration as in FIG. 31a.

FIG. 39b represents a front view of the cage of FIG. 39a.

FIG. 39c represents a back view of the cage of FIG. 39a.

FIG. 40b represents a back view of the cage of FIG. 40a.

FIG. 40c represents a perspective view of the diamond-shaped skeleton cage of FIG. 40a.

FIG. 44b represents a back view of the same cage configured as in FIGS. 41a and 44a.

FIG. 45b represents a back view of the same cage configured as in FIGS. 41b and 45a.

FIG. 47b represents a front view of the rotational element of FIG. 47a.

FIG. 48b represents a front view of the cage in the configuration of FIG. 48a.

FIG. 49b represents a front view of the cage in the second configuration of FIG. 49a.

FIG. 50b represents a front view of the cage in the configuration of FIG. 50a.

Figure 1:
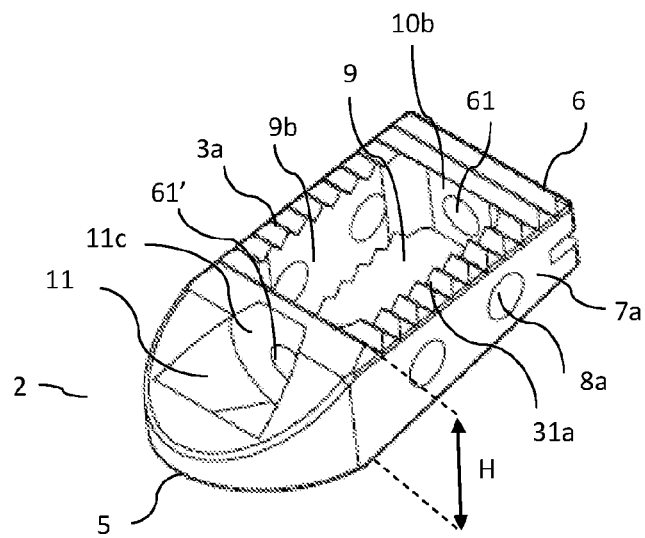
FIG. 1 represents a perspective view of the body of the cage of the first embodiment, without the rotational element.

According to FIGS. 1 to 6e, a first embodiment of the invention describes an interbody cage 1, for posterior, posterior-lateral, transforaminal, lateral or oblique approaches, with a body 2 having an elongated conventional shape for impactation cages, namely essentially parallelpipedal or with a lordotic angle. According to FIG. 1, the body 2 has one superior surface 3a which engages a superior vertebra 4a and one inferior surface 3b which engages an inferior vertebra 4b. The cage 2 has an anterior part 5 in the shape of a wedge and a flat posterior part 6. The two superior and inferior surfaces 3a, 3b are inclined relative to the medial horizontal plane of the body 2 so as to obtain a body 2 in which the height of the posterior part 6 is lower than a height H at the junction point between the large dimension of the wedged-shaped anterior part 5 and the superior and inferior surfaces 3a, 3b of the body 2. The surfaces 3a, 3b may be covered with crenellations 31a, 31b to prevent the cage 1 from migrating in the interbody space. The lateral sides 7a, 7b of the body 2 are essentially flat and contain openings 8a, 8b to allow lateral ingrowth of regenerating bone. The body 2 preferably contains a cavity 9 which may contain bone graft. This cavity 9 has two lateral inner-sides 9a, 9b, one anterior inner-side 10a, and one posterior inner-side 10b. A receiving cavity 11 is also arranged in the wedge-shaped anterior part 5 of the body 2 in order to receive the rotational element 12 of the invention.

Figure 2A:
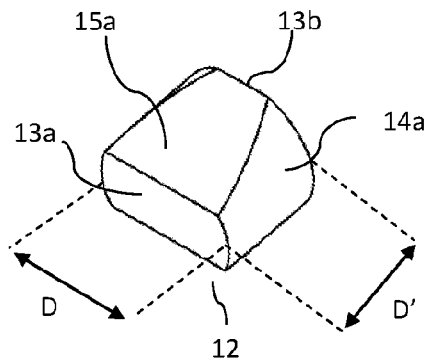
FIG. 2a represents a perspective view of the rotational element of the first embodiment without the body of the cage, in a first position.
Figure 2B:
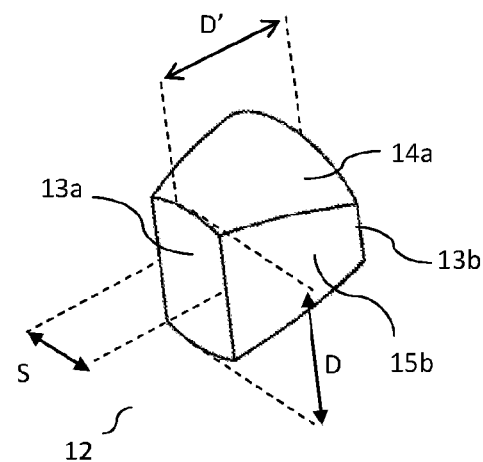
FIG. 2b represents a perspective view of the rotational element of the first embodiment without the body of the cage, in a second position.

According to FIGS. 2a and 2b, the rotational element 12, which is to be placed in the receiving cavity 11 of the body 2 of the cage, has a shape substantially matching that of the receiving cavity 11. The rotational element 12 has a long dimension D which is described in FIG. 2a as constant along the depth D' of the rotational element 12. FIG. 2a represents the rotational element 12 in its horizontal position, while FIG. 2b represents the same in a vertical position after a 90° rotation around its medial axis. The rotational element 12 has an anterior side 13a and posterior side 13b, the latter designed to engage the posterior surface 11c of the cavity 11. The distance between the anterior side 13a and the posterior side 13b of the rotational element 12 defines the depth D'. The lateral sides 14a, 14b of the rotational element 12 define the long dimension D and extend along the depth D'; they have the purpose of engaging the adjoining vertebrae, as described in FIGS. 6b and 6c after a rotation of the rotational element. The anterior side 13a of the rotational element 12 has a cross section with a long dimension corresponding to the long dimension D and a short dimension S. The short dimension S is not constant between the superior surface 15a and the inferior surface 15b of the rotational element 12 as these surfaces 15a, 15b follow the gradients of the wedge-shaped anterior part 5 of the body 2.

The superior 15a and inferior 15b surfaces of the rotational element 12 may also have different shapes than those shown in FIGS. 2a, 2b, such as being arranged in two parallel planes thus essentially giving the rotational element a flattened rectangular shape. They may also be curved inwardly between the lateral sides 14a, 14b, thus present two concave surfaces 15a, 15b. In yet another variation, the rotational element may also have the shape of two essentially parallel rods the respective outward looking sides of which are arranged to correspond to the lateral sides 14a, 14b of the rotational element 12, and be connected between them by one or more connecting members. In such variation, the inner homogenous block-like structure of the rotational element 12 of this first embodiment is not present, such that the rotational element 12 only has the outward looking sides of the rods defining the long dimension D and the depth D' to engage the adjoining vertebrae 4a, 4b.

The superior 15a and inferior 15b surfaces of the rotational element 12 may be arranged closer to each other than as described in FIGS. 3a to 5a, such that these surfaces are not even with the neighboring surfaces of the body around the receiving cavity 11. The superior and inferior surfaces 15a and 15b of the rotational element 12 may also be arranged with a larger distance between them than as described in FIGS. 3a to 5a, and may also have anchoring features such as spikes or crenels or grooves arranged on them. They may also be arranged with a pass-through cavity similar to cavity 9 to allow the stuffing of bone-graft.

The long dimension D is preferably constant along the depth D' of the two lateral sides 14a, 14b, defining two parallel planes relative to each other, but may also be defined in non-parallel planes converging towards the anterior side 13a or towards the posterior side 13b of the rotational element 12. These planes may also be non-linear planes and/or have gaps. According to FIGS. 2a, 2b and 5a, the lateral sides 14a, 14b of the element 12 are convex, but in other variations of this embodiment the lateral sides 14a', 14b' may also be concave or flat or be arranged in two inclined converging planes to create a wedge along the depth D'. The advantage of such lateral wedges is that they may allow a more stable trajectory of the cage 1 when, after the deployment of the rotational element 12, the cage 1 is inserted between two vertebrae 4a, 4b and slides on the two lateral wedges of the deployed rotational element 12. The lateral sides 14a, 14b may also be arranged to include one or several gullies along the same axis of the depth D'.

The long dimension D of the rotational element 12 is typically greater than the height H of the body 2 between its superior and inferior surfaces 3a, 3b at the point of their longest distance apart, but may also be shorter. The rotational element 12 is connected in its posterior part 13b to a rod 16 which crosses the posterior part 6 of body 2 on its longitudinal medial axis through a bore 61 and crosses the anterior inner-side 10a of the cavity 9 through another bore 61' to emerge on the posterior surface 11c of the cavity 11 and to engage the posterior side 13b of the rotational element 12. This rod 16 may be a component of the cage 1 or of a delivery system (not visible) for the cage 1. The rod 16 may be disconnected from the posterior side 13b of the rotational element and from the posterior part 6 of the body 2 through any technical means, such as unscrewing, in case the rod 16 and the bore 61 are arranged with compatible threaded portions.

Figure 3A:
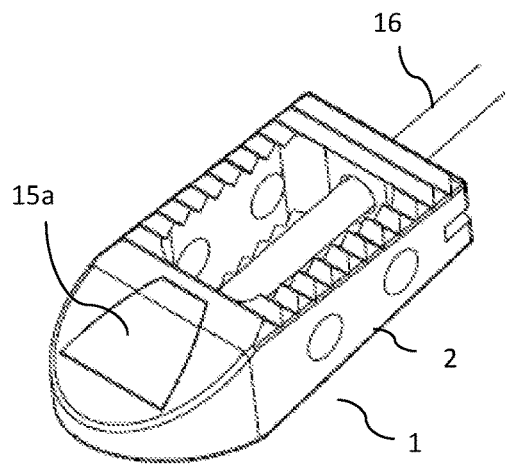
FIG. 3a represents a perspective view of the cage of the first embodiment with a non-deployed rotational element.

FIGS. 3a to 5b describe the cage 1 with its body 2 and rotational element 12 and rod 16, in three phases of the deployment of the rotational element 12. FIG. 3a describes the cage 1 with a non-deployed rotational element 12: only its superior surface 15a is visible. FIG. 4a describes the cage 1 after a rotation of approximately 45° of the rod 16 around its axis, which causes the superior surface 15a of the rotational element 12 to tilt and its lateral side 14a becomes partly visible. FIG. 5a describes the cage with the full deployment of the rotational element 12 after another rotation of the rod 16 of approximately 45°. Between the respective configurations shown in FIG. 3a and in FIG. 5a, the fully completed rotation of the rod 16 is approximately 90°.

Figure 3B:
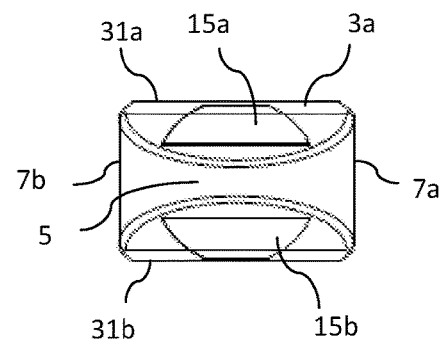
FIG. 3b represents a front view of the cage configured as in FIG. 3a with a non-deployed rotational element.
Figure 4A:
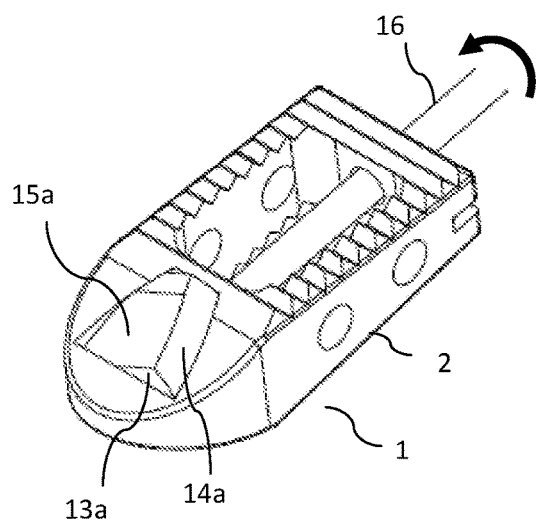
FIG. 4a represents the same perspective view of the cage of the first embodiment but with a semi-deployed rotational element.
Figure 4B:
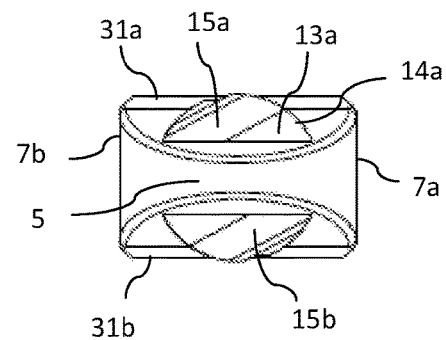
FIG. 4b represents a front view of the cage configured as in FIG. 4a with a semi-deployed rotational element.
Figure 5A:
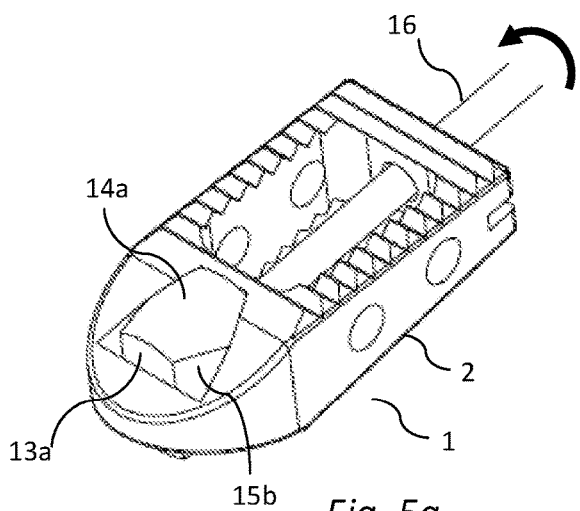
FIG. 5a represents the same perspective view of the cage of the first embodiment but with a fully deployed rotational element.
Figure 5B:
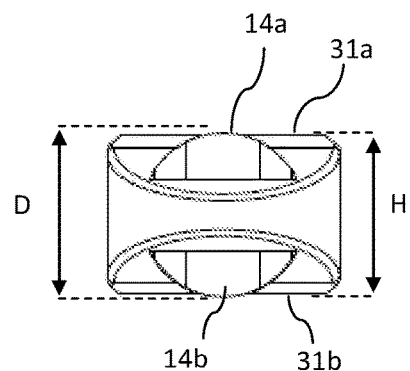
FIG. 5b represents a front view of the cage of FIG. 5a with a fully deployed rotational element.

FIGS. 3b, 4b and 5b provide a frontal view of the three respective configurations described in FIGS. 3a, 4a and 5a. According to FIG. 5b, when the rotational element 12 is rotated 90°, the long dimension D is greater than the highest height H between the superior and inferior surfaces 3a, 3b of the body 2 defined by the crenellations 31a, 31b.

Figure 6A:
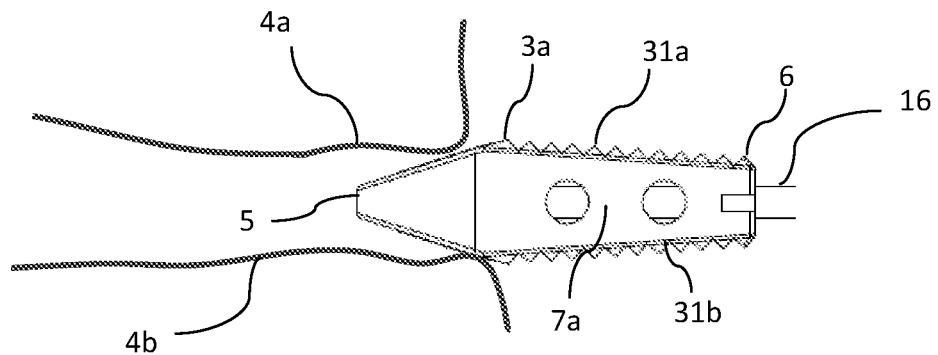
FIG. 6a represents a view of two schematic sections of two vertebral bodies and a cage viewed from its lateral side having its tip inserted between the vertebral bodies with a non-deployed rotational element.
Figure 6B:
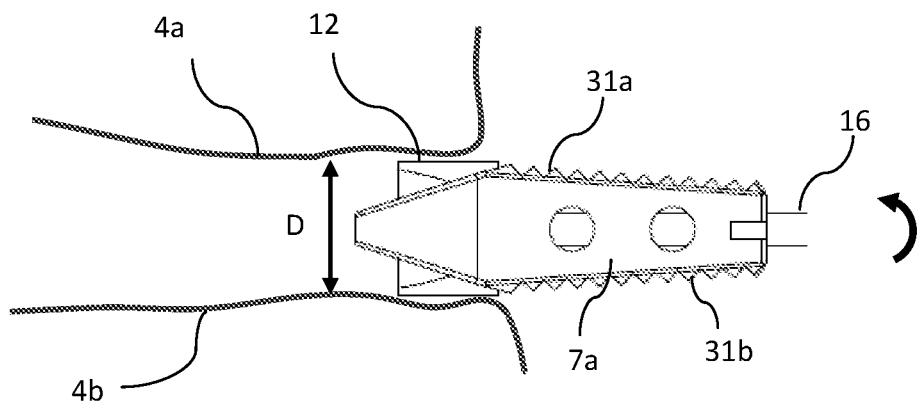
FIG. 6b represents the same view as in FIG. 6a, with a cage having a fully deployed rotational element.
Figure 6C:
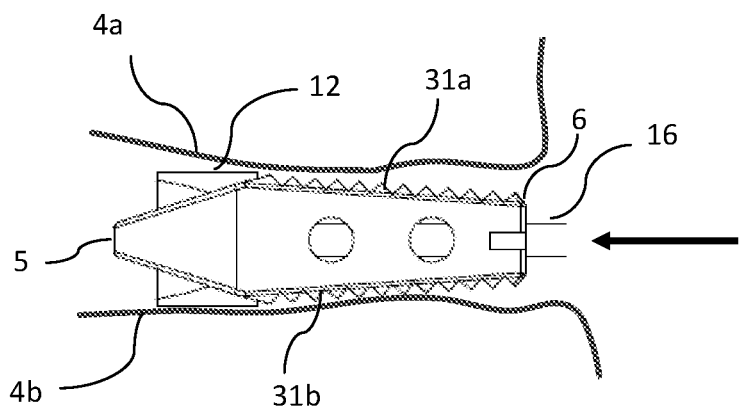
FIG. 6c represents the same view of two schematic sections of vertebral bodies as in FIGS. 6a and 6b, and a cage with a fully deployed rotational element having been entirely inserted between the two vertebrae.
Figure 6D:
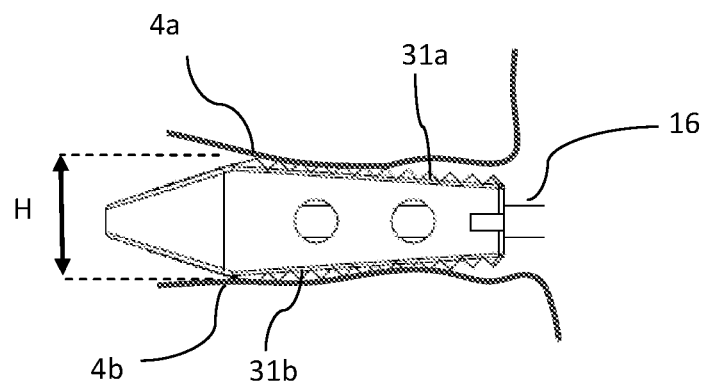
FIG. 6d represents the same view of the cage as in FIG. 6c, but with a non-deployed rotational element.
Figure 6E:
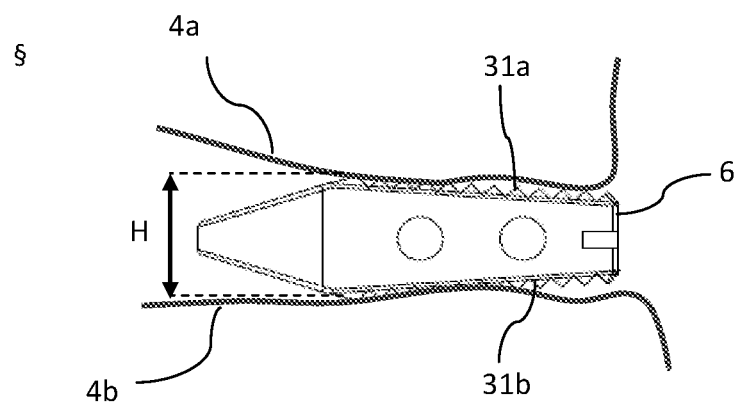
FIG. 6e represents the same view of the cage as in FIG. 6d, after removal of the delivery rod.

FIGS. 6a to 6e describe the method of the invention. According to FIG. 6a, the cage 1 is first introduced between two adjoining vertebrae 4a, 4b with the anterior part 5 of the body 2 only; preferably the full depth D' of the rotational element 12 is inserted, causing the entire superior and inferior surfaces 15a, 15b of the rotational element 12 to engage with the superior and inferior vertebrae 4a, 4b. The rod 16 is then actuated in rotation at an angle close to 90° around its axis which causes the rotational element 12 to rotate 90° relative to the planes of the superior and inferior surfaces 3a, 3b of the body 2. As described in FIG. 6b, this has the effect of expanding the intervertebral space between the two adjoining vertebrae 4a, 4b to a height equal to the long dimension D of the rotational element 12. The long dimension D is superior to height H of the highest portion between the superior and inferior surfaces 3a, 3b of the body 2. After this distraction of the intervertebral space is achieved at this dimension D, FIG. 6c shows how the cage 1 has been entirely pushed between the two vertebrae 4a, 4b gliding on the lateral sides 14a, 14b of the fully deployed rotational element 12. The advantage of the invention is that the lateral sides 14a, 14b distract the adjoining vertebrae 4a, 4b such that the crenellated superior and inferior surfaces 3a, 3b of the body 2 do not engage with the end plates of vertebrae 4a, 4b, or this contact is significantly reduced, so as not to obstruct the migration of the cage into the intervertebral space. According to FIG. 6d, the rotational element 12 is then rotated back into a horizontal position corresponding to the axial plane of the human body into the cavity 11 of the body 2, which removes the distraction force against the superior and inferior vertebra 4a, 4b and reduces the intervertebral space, thus causing the superior and inferior surfaces 3a, 3b of the body 2 to engage the superior and inferior vertebrae 4a, 4b to reach height H, at least at two engagement points of the intervertebral space. This rotation may also occur naturally merely by the pressure of the adjoining vertebrae once no force is applied to keep the lateral sides 14a, 14b of the rotational element 12 distracting the adjoining vertebrae 4a, 4b. The rod 16 may also be easily removed from the cage 1 after the final rotation, leaving the cage 1 in the intervertebral space as described in FIG. 6e. Instead of rotating back the rotational element 12, the second rotation may also be executed by pursuing the rotation in the same direction as in the first rotation, thus achieving a cumulative rotation of approximately 180°.

The interest of the invention is also to allow the later adjustment of the initial positioning of the cage 1 in the intervertebral space by reproducing the method. The cage 1 is in its position as described in FIG. 6d, with the rod 16 still connected to the body 2 of cage 1. A rotation is exerted on the rod 16 to cause the rotational element 12 to distract the intervertebral space between the two vertebrae 4a, 4b (as in FIG. 6b), and the cage 1 is pushed further forward or pulled back, or reinserted according to a different trajectory. After this adjusting motion, the counter-rotation is actuated to anchor the crenellations 31a, 31b into the vertebrae 4a, 4b.

As variations to this first embodiment and methods of insertion, the rotational element 12 may be rotated of an angle inferior to 90°, such as between 10° and 85° to distract the superior and inferior vertebrae 4a, 4b. This is possible if the lateral sides 14a, 14b are arranged further apart—and cavity 11 is enlarged accordingly —, such that the now longer dimension D does not require a full 90° rotation for the distraction of the vertebrae 4a, 4b in order to exceed height H. The anterior part 5 of the cage 1 may also be introduced into the intervertebral space by a distance inferior to the depth D' of the rotational element, such that not the full depth of the lateral sides 14a, 14b are engaging with the superior and inferior vertebrae 4a, 4b at the time of the rotation of the rotational element 12.

The plane defined by lateral sides 14a, 14b of the rotational element 12 along depth D' may also be curved along the axis of lateral sides 14a, 14b such that after the rotation of the rotational element 12 is completed (as in FIG. 6b), the cage 1 is pushed into the intervertebral space (as in FIG. 6c) according to a curved trajectory. This curved trajectory is facilitated when the lateral sides 14a, 14b of the rotational element 12 are arranged with lateral wedges along the axis of the depth D'.

The invention may also be practiced with a limited or no counter-rotation at all—and in this case, the rotational element 12 remains fully deployed; the vertebrae 4a, 4b engage both the lateral sides 14a, 14b of the rotational element 12 and the superior and inferior surfaces 3a, 3b of the body 2 in order to maintain the intervertebral space durably distracted also at the anterior part 5 of the cage 1 occupied by the rotational element 12. This deployment may be secured with a circular rim 38 arranged on one of the components fitting a circular groove 39 arranged on the other component, such is described in FIGS. 7d and 7e for a variation of the second embodiment.

The rotation of the rotational element 12 may be actuated through any other technical means not requiring a rod 16.

Figure 7A:
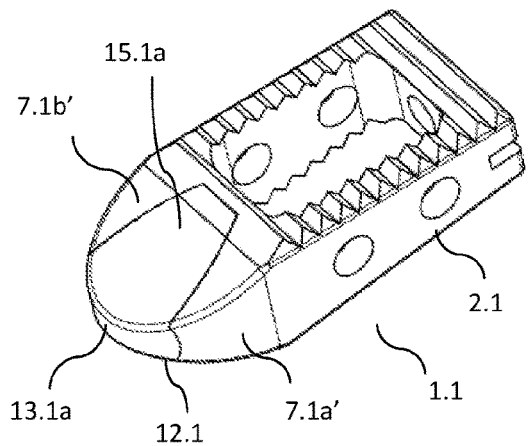
FIG. 7a represents a perspective view of an interbody cage of the second embodiment with a non-deployed rotational element.
Figure 7B:
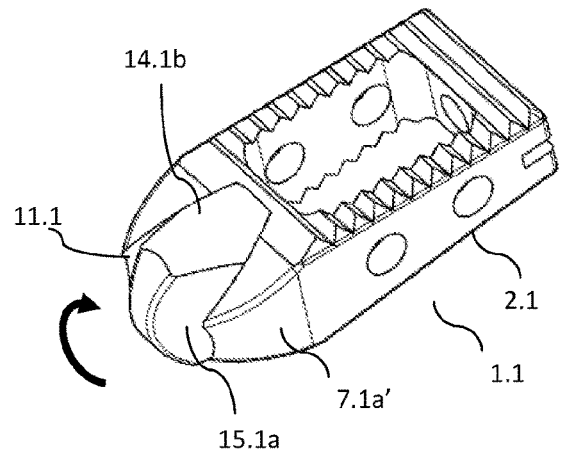
FIG. 7b represents the same perspective view of the cage of the second embodiment as in FIG. 7a but with a fully deployed rotational element.
Figure 7C:
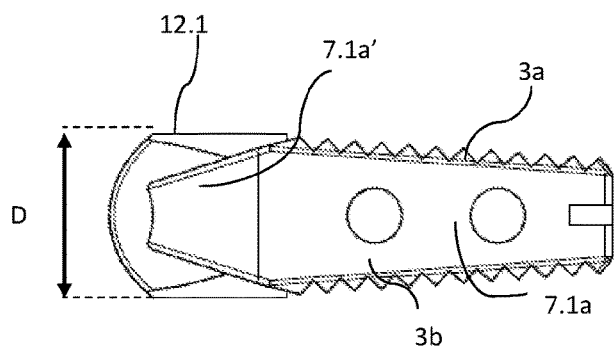
FIG. 7c represents a lateral view of the cage of the second embodiment with a fully deployed rotational element as in FIG. 7b.
Figure 7D:
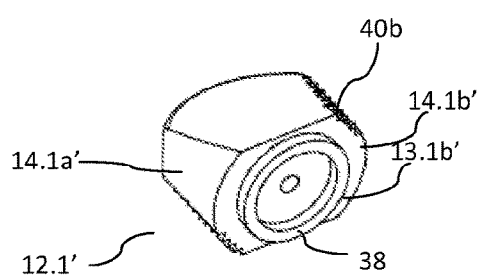
FIG. 7d represents a perspective view of the posterior side of the rotational element of the cage of the second embodiment with a large circular rim.
Figure 7E:
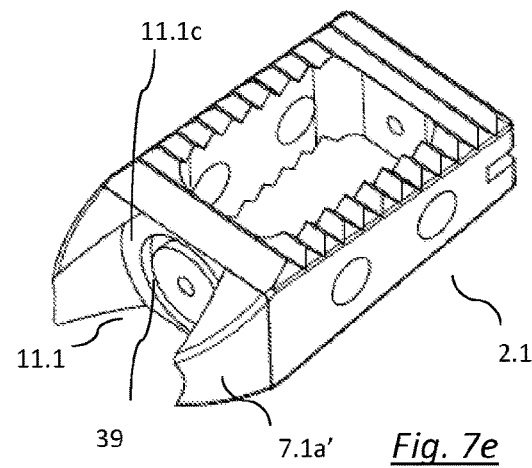
FIG. 7e represents a perspective view of the body of the cage of the second embodiment with a large circular groove.

A second embodiment of the invention is described in FIGS. 7a, 7b and 7c, describing a cage 1.1 with a body 2.1 arranged with a receiving cavity 11.1 flanked by two flanks 7.1a', 7.1b' and opened on the front side in order to receive a rotational element 12.1 and allow the anterior side 13.1a of the rotational element to protrude beyond the ends of the flanks 7.1a', 7.1b'. The wedge-shaped rotational element 12.1 occupies most of the volume of the anterior part 5.1 of the body 2.1, and may be connected to the body 2.1 through any technical means such as a hollow bolt allowing the throughput of the rod 16. As described in FIG. 7c, once the rotational element 12.1 is rotated 90°, the long dimension D of rotational element 12.1 exceeds the height H of the body 2.1 at its highest section between the superior and inferior surfaces 3a, 3b of the body 2.1. The advantage of this embodiment is that the wedge-shaped superior surfaces 15.1a, 15.1b and the lateral sides 14.1a, 14.1b offer a longer surface for engaging the vertebrae 4a, 4b. A variation of this second embodiment is to arrange a flat (instead of curved) anterior side 13.1a of the rotational element, and/or remove the flanks 7.1a', 7.1b' which are flanking the cavity 11.1. Another variation consists in replacing the wedge-shaped surfaces 15.2a, 15.1b with a first portion of the depth D', starting from the anterior side 13.1a in the shape of two essentially parallel surfaces 15.2a, 152b (thus defining a flattened rectangular shape), suitable to be introduced between two slightly distracted vertebrae, and as second convex portion of depth D' connecting the back-side circumference of the first portion of the rotational element 12.1 with the circumference of the posterior side 13.1*b* of the rotational element 12.1.

The rotational element 12.1 and body 2.1 of the second embodiment may also be arranged so that the rotational element 12 remains durably deployed between the vertebrae 4*a*, 4*b* after the insertion of the cage 1.1 and the rotation of the rotational element 12. According to a variation shown in FIG. 7*d*, a circular rim 38 may be arranged on the posterior side 13.1*b*' of the rotational element 12.1' to engage with a circular groove 39 of a compatible cross-section, arranged on the posterior inner-side 11.1*c* of the receiving cavity 11.1 of the body 2.1, as described in FIG. 7*e*. The radiuses of the circular rim and of circular groove—essentially of a similar distance—may vary. The advantage of a large radius of the circular rim 38 engaged in a circular groove 39 with similar large radius, is to provide stability to the rotational element 12.1' for it to remain deployed. The potential oblique pressure exercised by the vertebrae 4*a*, 4*b* on the lateral sides 14.1*a*', 14.1*b*' of the deployed rotational element 12.1' which may otherwise cause the rotational element 12.1' to flip, are avoided or at least mitigated. Any other technical means to secure the rotational element 12.1' in a deployed position relative to the body 2.1' may be applied, such as pulling back the rotational element 12.1 thus allowing for a protruding portion arranged on its posterior side 13.1*b*' to engage into a recess arranged in the posterior inner-side 11*c* of the receiving cavity 11.1. Another means is to arrange a rack-and-pinion component, or as another example, the design of cage 1.1" described in FIGS. 31*a*, 31*b* and 31*c*. The circular rim 38 may also be arranged on the posterior inner-side 11.1*c* of the receiving cavity 11.1 of the body 2.1 to fit a circular groove 39 arranged on the posterior side 13.1*b*' of the rotational element 12.1'.

Figure 8:
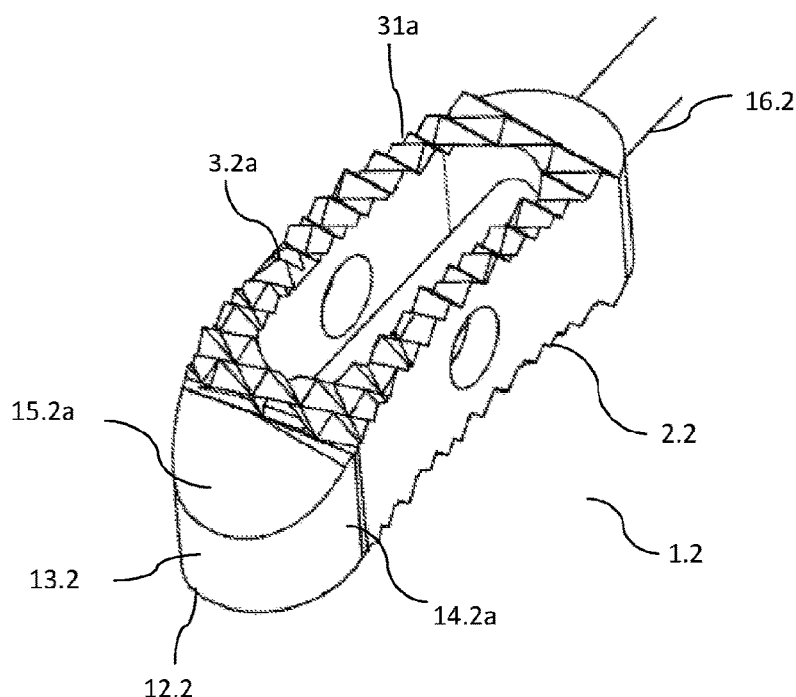
FIG. 8 represents a perspective view of a crescent-shaped interbody cage according to the third embodiment.
Figure 9:
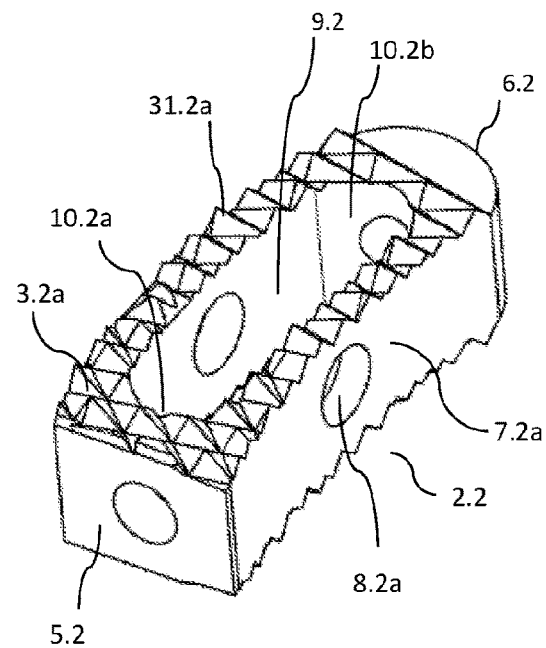
FIG. 9 represents a perspective view of the body of the cage of the third embodiment represented in FIG. 8, without the rotational element.
Figure 10:
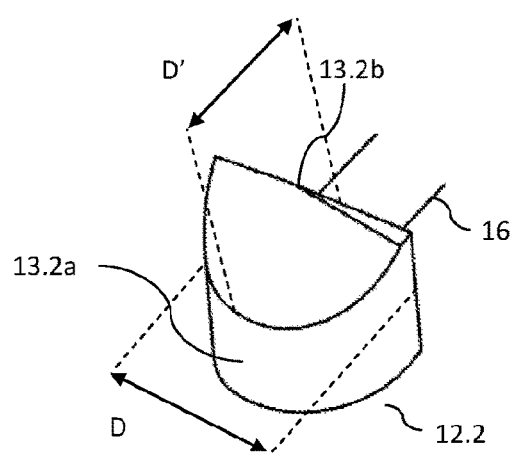
FIG. 10 represents a perspective view of the rotational element of the cage of the third embodiment represented in FIG. 8.
Figure 11:
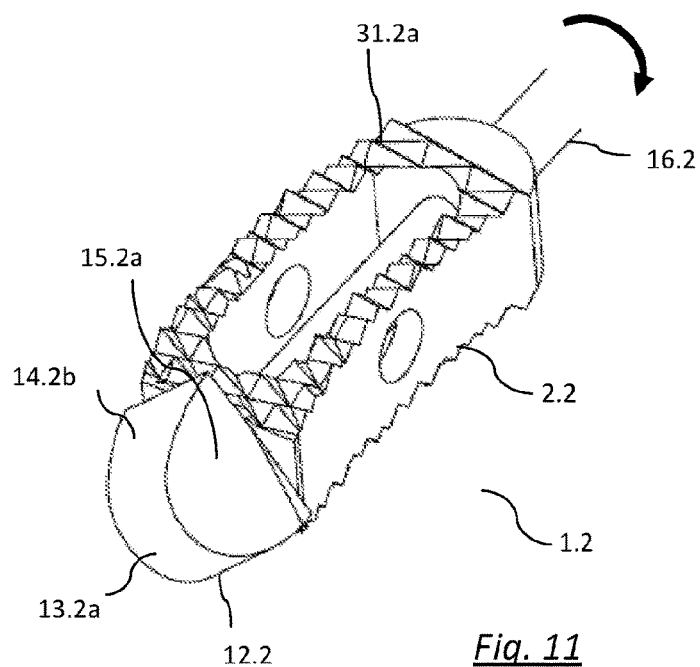
FIG. 11 represents the same perspective view of the cage in FIG. 8 but with a semi-deployed rotational element.
Figure 12A:
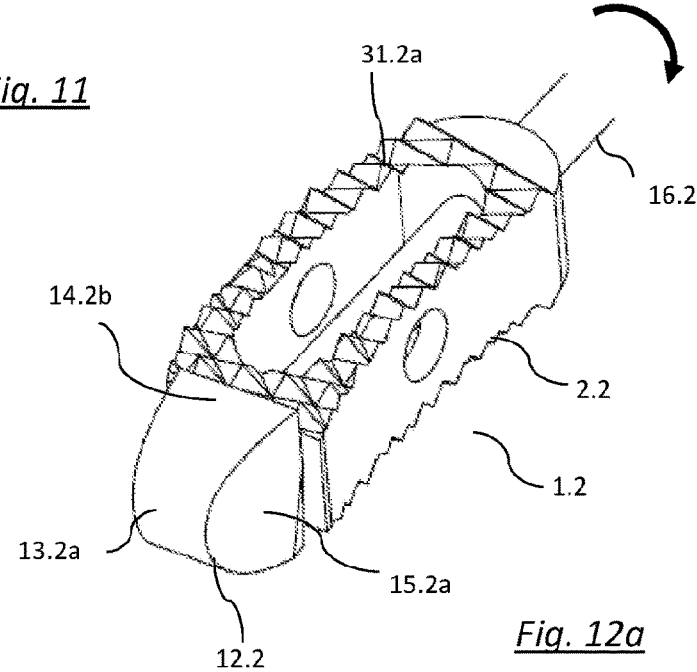
FIG. 12a represents the same perspective view of the cage in FIGS. 8 and 11 but with a fully deployed rotational element.

FIGS. 8, 11, and 12*a* describe the third embodiment of the invention, wherein the cage 1.2 is arranged with a rotational element 12.2 covering the entire anterior part 5.2 of the body 2.2 of the cage 1.2. According to FIG. 9 the cage 1.2 has a crescent-shaped body 2.2, which is an advantageous shape for transforaminal surgical approaches. The superior and inferior surfaces 3.2*a*, 3.2*b* of the body 2.2 are laterally angled relative to one another: the distance between the superior and inferior surfaces 3.2*a*, 3.2*b* on the lateral side 7.2*b* of the body is longer than the distance between the superior and inferior surfaces 3.2*a*, 3.2*b* on the other lateral side 7.2*a* of the body 2.2. The body 2.2 also has an anterior part 5.2 and a posterior part 6.2, and cavities for bone ingrowth 8.2*a*, 8.2*b*, 9.2. The anterior part 5.2 of the body 2.2 is essentially flat. FIG. 10 describes a rotational element 12.2, the posterior side 13.2*b* of which is arranged to engage with the anterior part 5.2 of the body 2.2. According to FIG. 10, the anterior and posterior sides 13.2*a*, 13.2*b* of the rotational element 12.2 are not arranged in parallel planes and instead, the long dimension D is defined at the tipping point of the posterior side 13.2*b* of the rotational element 12.2. The lateral sides. 14.2*a*, 14.2*b* of the rotational element 12.2 converge along two convex curves towards the anterior side 13.2*a* of the rotational element 12.2 defining depth D', as described in FIG. 12*b*. The long dimension D essentially corresponds to the distance between the two lateral sides 7.2*a* and 7.2*b* of the body 2.2 at its anterior part 5.2. In different variations of this third embodiment, the long dimension D may be greater than the distance between the two lateral sides 7.2*a* and 7.2*b* of the body 2.2 at its anterior part 5.2.

Figure 12B:
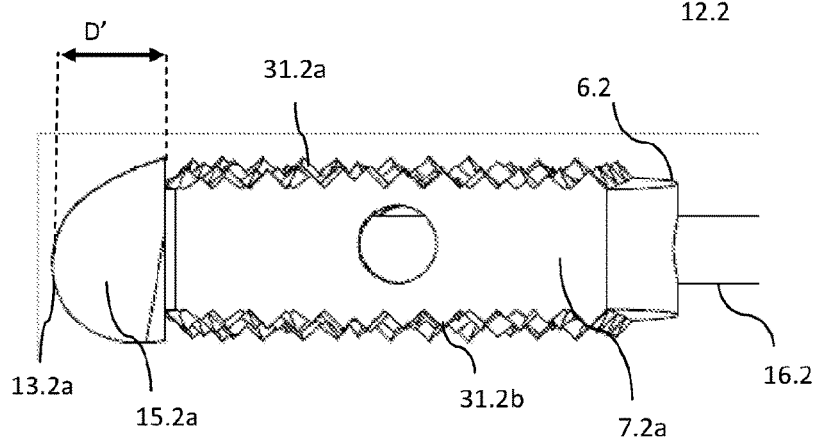
FIG. 12b represents a lateral view of the cage in FIG. 12a with a fully deployed rotational element.

The insertion of cage 1.2 according to this third embodiment is similar to the one described in FIGS. 6*a* to 6*e* for the first embodiment. FIG. 8 describes the cage 1.2 with a non-deployed rotational element 12.2, which is typically the configuration for the first insertion step of the cage 1.2 (corresponding to the step described in FIG. 6*a* for the first embodiment) and for the final configuration of the cage 1.2 once it is in its final position (also comparable to the description in FIGS. 6*d* and 6*e* for the first embodiment). FIG. 11 describes the cage 1.2 with a semi-deployed rotational element 12.2, during the rotation process. FIGS. 12*a* and 12*b* describe the cage 1.2 with a fully deployed rotational element 12.2, to achieve the maximum distraction of the adjoining vertebrae 4*a*, 4*b* (corresponding to the step described in FIG. 6*b* for the first embodiment) and for the full introduction of the cage 1.2 (corresponding to the step described in FIG. 6*c* for the first embodiment).

There are several possible variations of the characteristics of the rotational elements 12.1 and 12.2 of the second and third embodiments, for instance where the long dimension D is shorter than the height H between the crenellated superior and inferior surfaces 3.1*a*, 3.1*b*, 3.2*a*, 3.2*b* of the body 2.1, 2.2, or where the lateral sides 14.2*a*, 14.2*b* of the rotational element 12.2 extend beyond the lateral sides 7.2*a*, 7.2*b* of the body 2.2 such that the long dimension D exceeds the width of the body 2.2. The anterior side 13.1*a*, 13.2*a* of the rotational element 12.1, 12.2 may also have various shapes such as be bullet-nosed, or have a flat or concave shape.

FIGS. 13 14*a* and 14*b* describe a fourth embodiment of the invention, where the rotational element 12.3 is extended along a portion of the superior surface 3.3*a* of the body 2.3 towards the posterior part 6.3 of the body 2.3 of the cage 1.3 along one lateral side 7.3*b* of the body 2.3. This mobile surface 17*a* of the rotational element 12.3 has the advantage to offer a longer depth D' of the rotational element 12.3 on one of its lateral sides 14.3*b* compared to the short depth D' of the rotational element 12.2 of the third embodiment. The load bearing surface 18*a* of the rotational element 12.3 is increased and the force bearing against the superior vertebrae 4*a* distributed on a longer depth D', while the cage is pushed into the intervertebral space after the rotation of the rotational element.

The introduction of this cage 1.3 is executed according to the same method as described in FIGS. 6*a* to 6*e* for the first embodiment: the anterior part 13.3*a* of the rotational element 12.3 is first introduced between the two vertebrae 4*a*, 4*b* in a horizontal position; the rotational element 12.3 is rotated through actuation of the rod 16.3, and its lateral sides 14.3*a* and 14.3*b* engage the respective adjoining vertebrae 4*a*, 4*b* and the load bearing flank 18*a* engages the superior vertebra 4*a*. The cage 1.3 is then pushed into the intervertebral space with its deployed rotational element 12.3, with the load bearing flank 18*a* of the mobile surface 17*a* protecting the vertebra 4*a* against the abrasion of the crenellations 31.3*a* arranged on the superior surface 3.3*a* of the body 2.3. Once the cage 1.3 is in its final position, a counter-rotation is actuated in the opposite direction to the initial rotation, and the inferior side of mobile surface 17*a* engages with the body 2.3 again, as in FIG. 13. The rod 16.3 or other appropriate delivery system is removed from the cage 1.3. The position of the cage 1.3 may also be corrected by redeploying the rotational element 12.3 through a rotation, and the cage 1.3 is then pushed forward or pulled back, or its position is adjusted along a new axis, before the counter-rotation is executed again.

As variation of the fourth embodiment, the rotational element 12.3 may also be arranged on a symmetrical cage similar to the cages 1 and 1.1 described in FIGS. 3a and 7a, and/or where the rotational element 12.3 is prolonged by one mobile surface 17a as described in FIGS. 13, 14a and 14b and also by one second mobile surface 17b arranged on the inferior surface 3.3b of the body 2.3, diagonally, on the opposite side from the mobile surface 17a of the superior surface 3.3a of the body 2.3. This second mobile surface 17b may be arranged symmetrically, with a load bearing flank 18b on the inferior mobile surface 17b being similar in shape and length to the load bearing flank 18a of the mobile surface 17a, or asymmetrically, with different lengths and widths between the mobile surfaces 17a and 17b and load bearing flanks 18a and 18b, respectively.

Figure 15A:
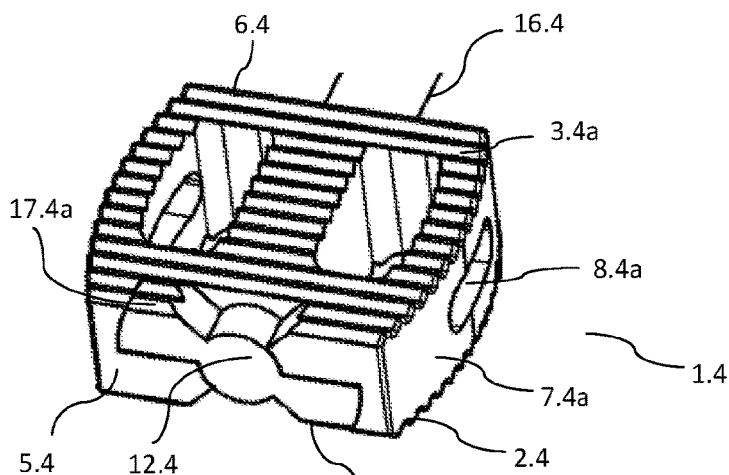
FIG. 15a represents a perspective view of an interbody cage of the fifth embodiment for anterior cervical or anterior lumbar approaches with a non-deployed rotational element.
Figure 15B:
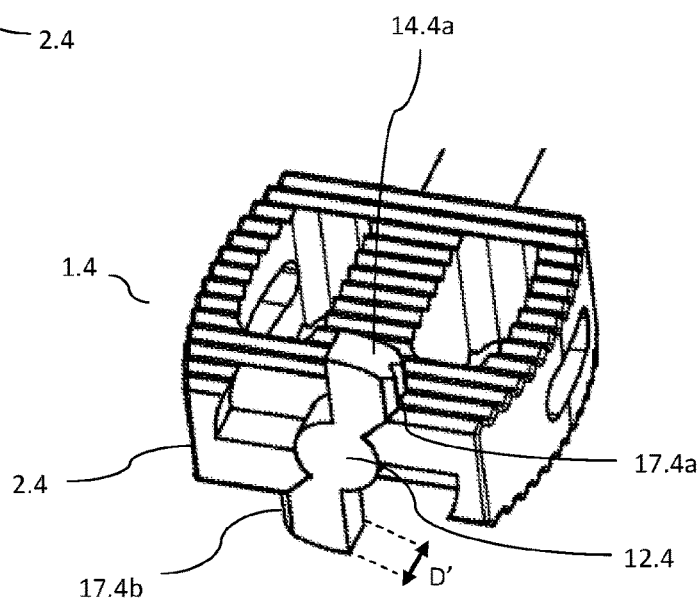
FIG. 15b represents the same perspective view of the cage as in FIG. 15a but with a fully deployed rotational element.

FIGS. 15a and 15b describe a fifth embodiment of the invention where a cage 1.4 designed for anterior cervical or anterior lumbar approaches comprises a rotational element 12.4 arranged on the anterior part 5.4 of the body 2.4 which body has a lower height than the height H of the posterior part 6.4 of the cage 1.4. The rotational element 12.4 of this embodiment is in the shape of a segmented helix, each segment serving as prolongation of a section of the superior and inferior surfaces 3.4a, 3.4b at the anterior part 5.4 of the body 2.4. In this embodiment, the anterior part 5.4 of the cage has a section of its superior and inferior surfaces 3.4a, 3.4b replaced by symmetrically arranged mobile surfaces 17.4a, 17.4b centrally connected in the rotational element. These mobile surfaces 17.4a, 17.4b have the same functions as the mobile surface 17a of the fourth embodiment. The rotational element 12.4 has lateral sides 14.4a, 14.4b defining the long dimension D as in the first to fourth embodiments. The depth of the lateral sides 14.4a, 14.4b of the mobile surfaces 17.4a, 17.4b, defines the depth D' of the rotational element 12.4. The long dimension D does not necessarily need to be equal or greater than the height H of the highest dimension of the body 2.4, and may be smaller, due to the natural angled opening of the lumbar and cervical anterior spine.

The method of insertion of the cage 1.4 is similar to the one described in FIGS. 6a to 6e for the first embodiment: the anterior part 5.4 of cage 1.4 is first introduced between the vertebrae 4a, 4b preferably until the depth D' of the lateral sides 14.4a, 14.4b of the rotational element is positioned in the intervertebral space, The rod 16.4 is rotated, which deploys the rotational element 12.4 and distracts the vertebrae 4a, 4b. The cage 1.4 is fully pushed into the intervertebral space on the lateral sides 14.4a, 14.4b of the rotational element 12.4. The counter-rotation is executed, and the superior and inferior surfaces 3.4a, 3.4b of the body 2.4 engage with the vertebrae 4a, 4b. The means to rotate the rotational element 12.4 may remain in the cage 1.4 or the rod 16.14 or any other delivery system may be removed.

Figure 16A:
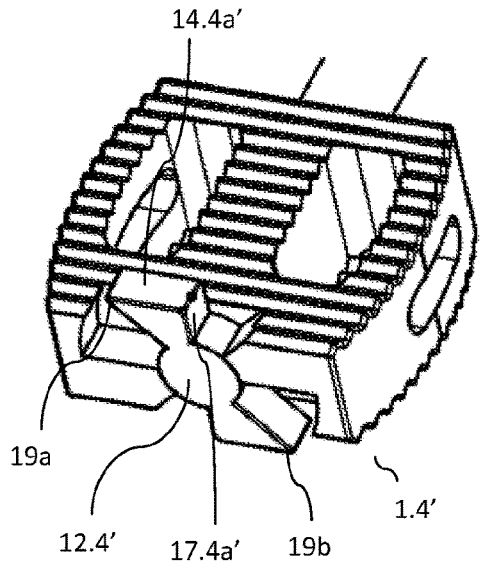
FIG. 16a represents a perspective view of an interbody cage of a variation of the fifth embodiment with a semi-deployed rotational element after a rotation of approx. 45°.
Figure 16B:
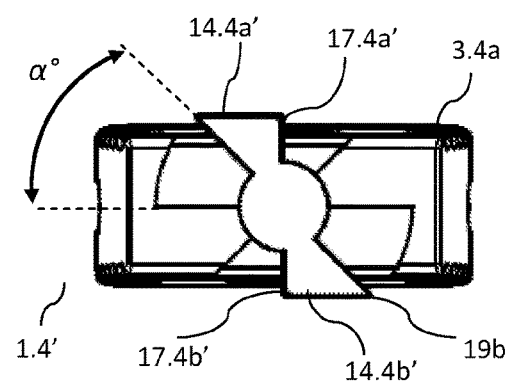

FIGS. 16a and 16b describe a variation of the fifth embodiment, wherein the parallel lateral sides 14.4a', 14.4b' and the mobile surfaces 17.4a', 17.4b' have an obtuse angle relative to each other, such that the rotation and counter-rotation do not need to be completed at 90°. In FIGS. 16a and 16b, the rotations of the rotational element 12.4' are executed at an angle α° of approximately 45°. This angle α° of rotation in these variations may also be smaller, such as between 25° to 35°, or, depending on the obtuse angle arranged between the lateral sides 14.4a', 14.4b' and the mobile surfaces 17.4a', 17.4b', higher, up to 85° to 90°. In this variation, the long dimension D may also be defined by the distance between the external edges 19a, 19b of the lateral sides 14.4a', 14.4b', wherein a rotation of the rotational element 12.4 exceeding the angle α° in FIGS. 16a and 16b, will cause these external edges 19a, 19b to engage the vertebrae 4a, 4b and further distract them.

Additional variations of this fifth embodiment are to arrange the rotational element 12.4, 12.4' in a receiving cavity 11.4 arranged in the anterior part 5.4, 5.4' of the body 2.4, 2.4' as in the first embodiment, or to arrange a wedged or bullet-nosed tip to the rotational element 12.4, 12.4' similar to tip 13.1a of the rotational element 12.1 of the second embodiment or tip 13.2a of the rotational element 12.2 of the third embodiment.

FIGS. 17a to 17d describe a cage 1.5 of the sixth embodiment of the invention, with a rotational element 12.5 having two smooth mobile surfaces 17.5a, 17.5b inspired from the mobile surface 17a of the fourth embodiment. As described in FIG. 17b, in the sixth embodiment, the smooth mobile surfaces 17.5a, 17.5b are carved out of the superior and inferior surfaces 3.5a, 3.5b of the body 2.5.

Figure 17A:
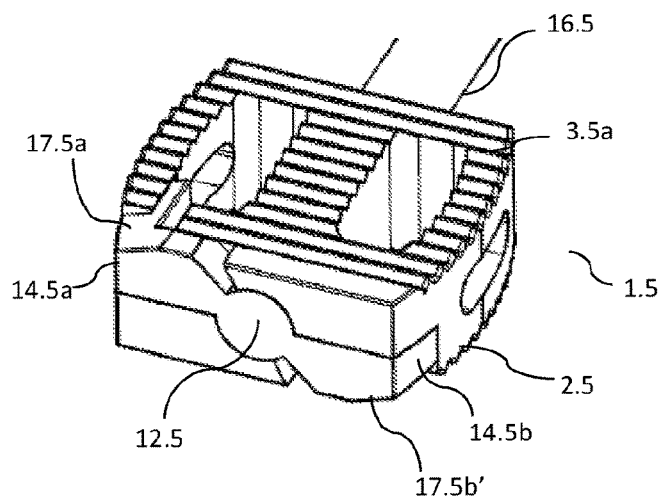
FIG. 17a represents a perspective view of an interbody cage of the sixth embodiment for anterior cervical or lumbar approaches with a non-deployed rotational element with laterally extending mobile surfaces.
Figure 17B:
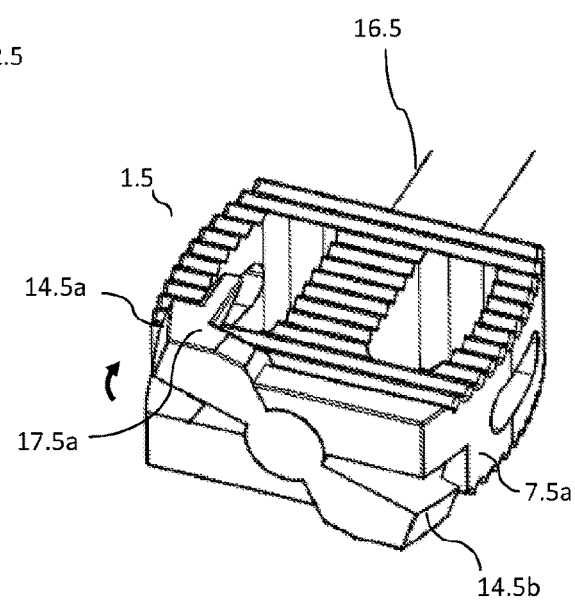
FIG. 17b represents the same perspective view of the cage as in FIG. 17a but with a deployed rotational element.
Figure 17C:
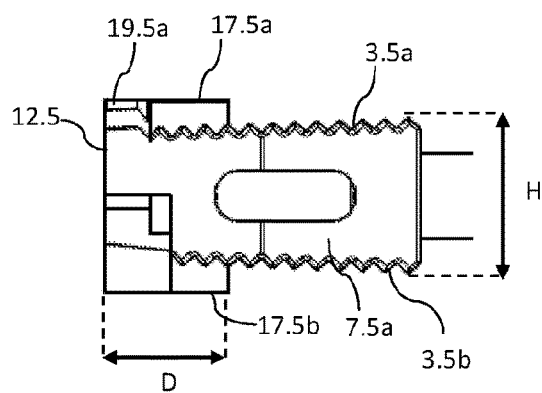
FIG. 17c represents a lateral view of the cage in the configuration of FIG. 17b.
Figure 17D:
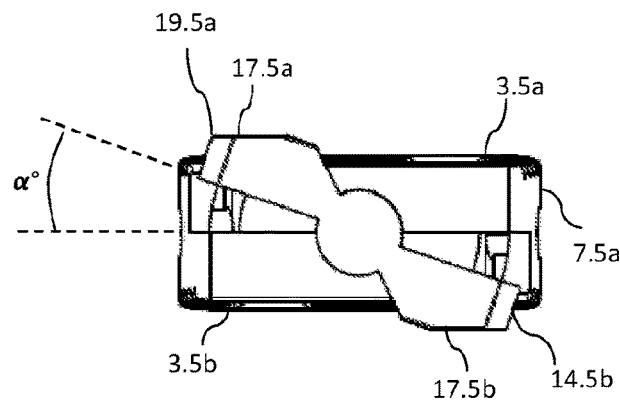
FIG. 17d represents a front view of the cage in the configuration of FIGS. 17b and 17c.

In this sixth embodiment, the long dimension D of the rotational element 12.5, may be as long as the distance between the edges 19.5a, 19.5b of the respective lateral sides 14.5a, 14.5b. As shown in FIG. 17c, due to the extended mobile surfaces 17.5a, 17.5b, the depth D' of the cage 1.5 may be much longer than the depth D' of the cage 1.4' of the fifth embodiment. In order to distract the vertebrae 4a, 4b of a distance superior to the maximum height H of the cage 1.5 (located at the posterior side 6.5 of the cage 1.5), the angle needed depends on the ratio between the potential long dimension D and the height H. Such angle may be much smaller than the 45° of angular rotation described for cage 1.4' of the fifth embodiment in FIG. 16b. According to FIG. 17d, the cage 1.5 of sixth embodiment has an angle α° of approx. 20 degrees. Given the low lordotic angle of the cage 1.5 and the buffer shown in FIG. 17c, the angulation could be even less than 20°, such as between 5° and 20°.

According to other variations of this sixth embodiment, the lateral sides 14.5a, 14.5b and mobile surfaces 17.5a, 17.5b of the rotational element 12.5 may, instead of defining parallel planes along the depth D' axis, be arranged in two planes that are converging towards the anterior part 5.5 of the cage 1.5 in such a way that when the rotational element 12.5 is deployed and the lateral sides 14.5a, 14.5b, engage the vertebrae 4a, 4b, the insertion of the cage 1.5 into the intervertebral space causes a further distraction of the interbody space following the gradients arranged on the mobile surfaces 17.5a, 17.5b.

Additional variations of this sixth embodiment may consist in arranging asymmetrically mobile surfaces 17.5a, 17.5b on a rotational element 12.5, or to arrange a rotational element 12.5 with only one mobile surface 17.5a on the superior surface 3.5a of the anterior part 5.5 of the cage 1.5 or its inferior surface 3.5b.

In variations of the fifth and sixth embodiments, the rotational element 12.4, 12.4', 12.5 may be arranged on either of the lateral sides 7.4a, 7.5a and/or 7.4b, 7.5b, of the body 2.4, 2.4', 2.5, which may be suitable for lateral surgical approaches.

The characteristics of the rotational elements 12.4, 12.4', 12.5 in the shape of a segmented helix of the fifth and sixth embodiment may also be applied to the other embodiments of the invention.

FIGS. 18a to 20b describe a seventh embodiment of the invention of an interbody cage 1.6 typically used for postero-lateral, transforaminal, oblique or lateral surgical approaches, which is arranged with an rotational element 12.6 which has the same characteristics as the rotational element 12 of the first embodiment, but is connected to two opposing extended members 20a, 20b at their proximal ends 21a, 21a', such extended members 20a, 20b, being also connected at their distal ends 21b and 21b' to the rod 16.6 in the posterior part 6.6 of the body 2.6 of the cage 1.6. The extended members 20a, 20b are lodged in slits 22a, 22a', 22b, 22b', arranged on the superior and inferior surfaces 3.6a, 3.6b of the body 2.6 on its anterior part 5.6 and posterior part 6.6. The advantage of this seventh embodiment is to extend the depth D' of the rotational member 12.6 along the whole length of the body 2.6 of the cage and to shield the vertebrae 4a, 4b from the abrasion of the crenellations 31.6a, 31.6b on the superior and inferior surfaces 3.6a, 3.6b of the body 2.6.

Figure 20A:
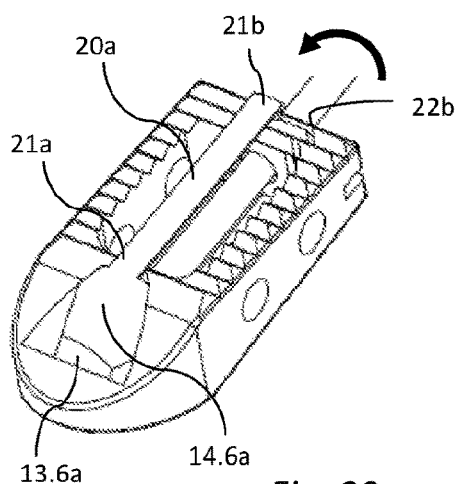
FIG. 20a represents a perspective view of the same symmetrical interbody cage of FIGS. 18a and 19 with a fully deployed rotational element prolonged by two elongated arcs.
Figure 20B:
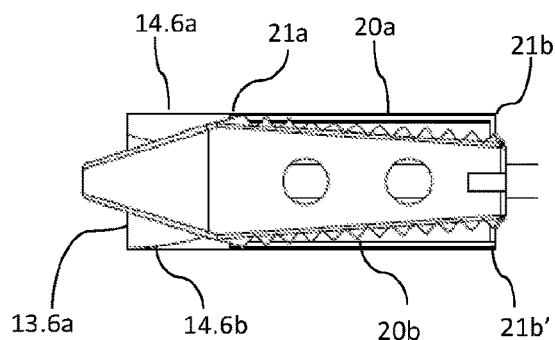
FIG. 20b represents a lateral view of the cage in the configuration of FIG. 20a with a fully-deployed rotational element prolonged by two elongated arcs.
Figure 21A:
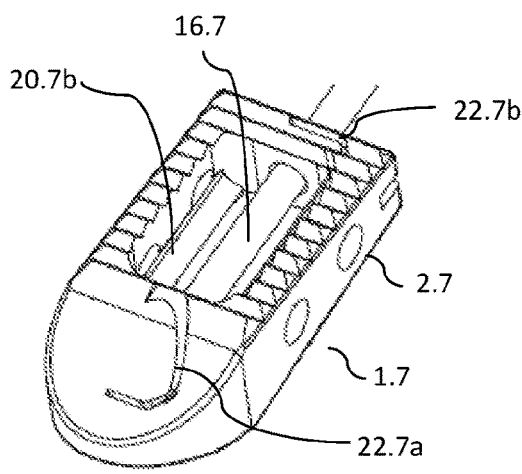
FIG. 21a represents a perspective view of a symmetrical interbody cage of the eighth embodiment with a non-deployed rotational element consisting of two opposing and connected elongated arcs.
Figure 21B:
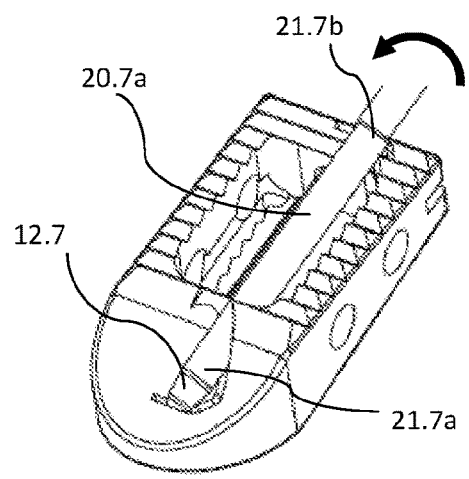
FIG. 21b represents a perspective view of the same symmetrical interbody cage of FIG. 21a but with semi-deployed elongated arcs.
Figure 22A:
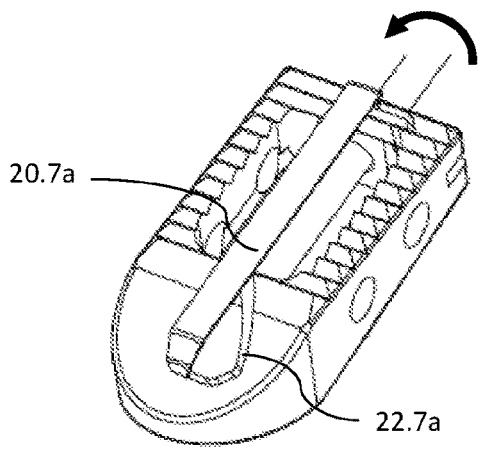
FIG. 22a represents a perspective view of the same symmetrical interbody cage of FIGS. 21a and 21b but with two fully deployed elongated arcs.
Figure 22B:
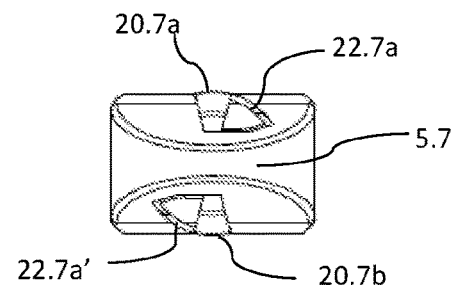
Figure 22C:
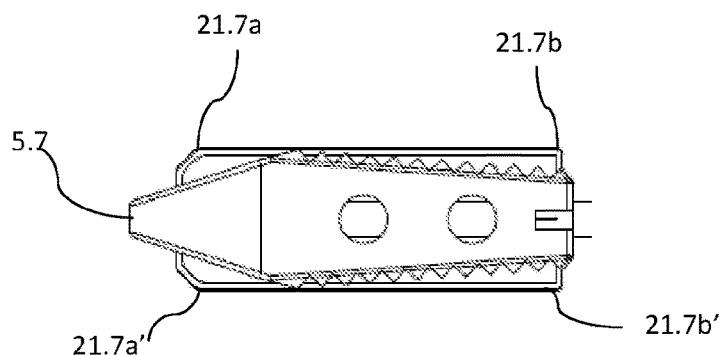
FIG. 22c represents a lateral view of the cage in the configuration of FIGS. 22a and 22b with fully deployed elongated arcs.
Figure 23A:
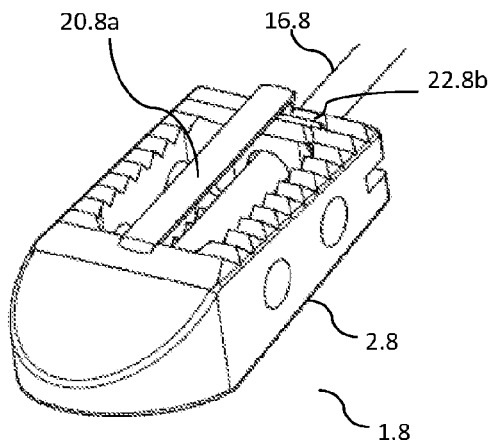
FIG. 23a represents a perspective view of a cage according to the ninth embodiment with a fully deployed shielding component in the shape of two symmetrically opposing arcs.
Figure 23B:
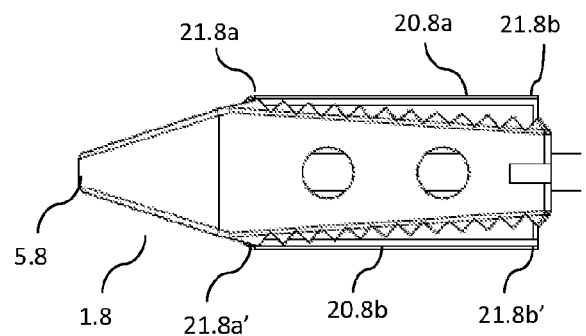
FIG. 23b represents a lateral view of the cage in the same configuration as in FIG. 23a with a fully deployed shielding component.
Figure 24A:
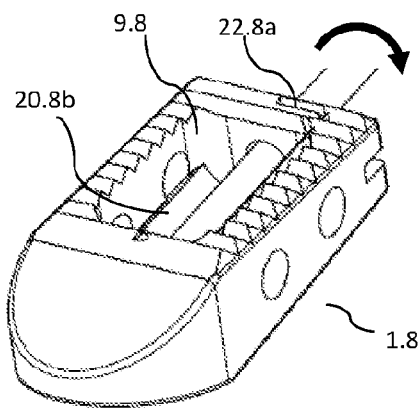
FIG. 24a represents a perspective view of the same cage as in FIGS. 23a and 23b but with a collapsed shielding component.
Figure 24B:
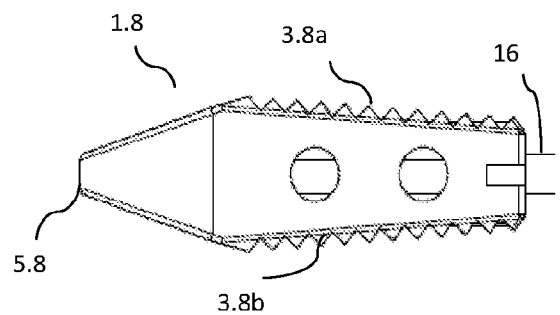
FIG. 24b represents a lateral view of the cage in the same configuration as in FIG. 24a with a collapsed shielding component.

The method of insertion of the cage 1.6 of the seventh embodiment follows similar steps to those of the first to sixth embodiments as described in FIGS. 6a to 6e. FIG. 20a describes that the connection point of the extended member 20a at its proximal end 21a with the posterior side 13.6b of the rotational element 12.6 is not aligned with the medial plane of the rotational element 12.6 defined by its lateral sides 14.6a, 14.7b. In such a configuration, the rotational element 12.6 does not need to be rotated 90°, as the shielding effect of the extended member 20a, 20b is actuated already before the rotational element 12.6 is fully deployed, as shown in FIGS. 20a and 20b. Depending on the length D of the long dimension arranged for the rotational element 12.6 compared to the height H of the longest dimension of the height of the body 2.6 of the cage 1.6, the rotation sufficient to deploy the rotational element may not need to be of 90°, but could be between 10° and 85°.

Figure 18A:
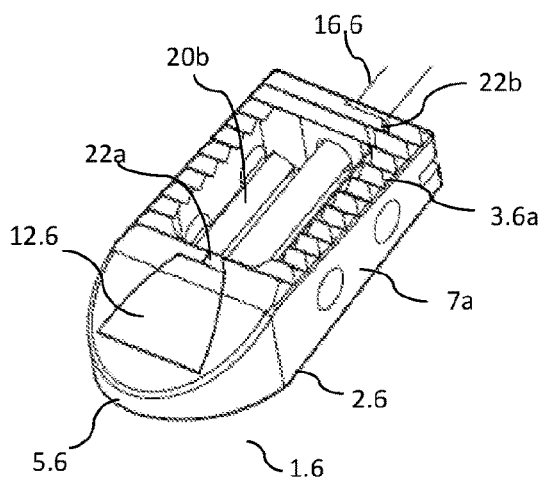
FIG. 18a represents a perspective view of a symmetrical interbody cage of the seventh embodiment with a non-deployed rotational element prolonged by two elongated arcs.
Figure 18B:
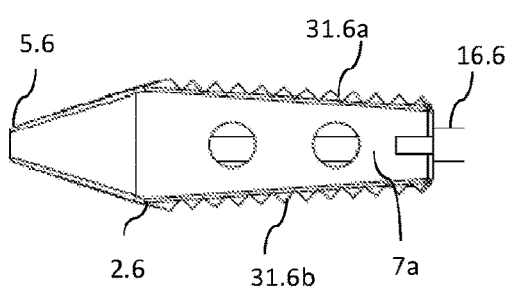
Figure 19:
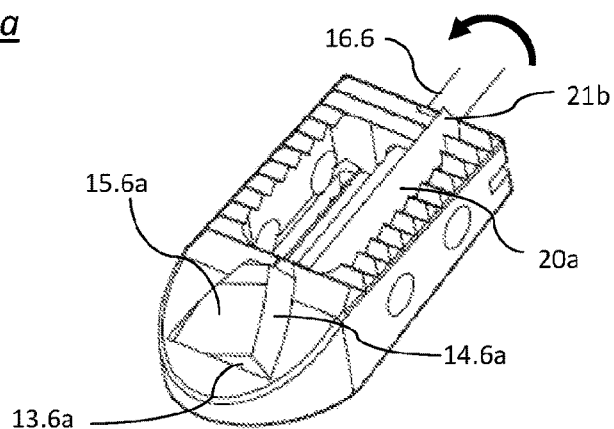
FIG. 19 represents a perspective view of the same symmetrical interbody cage of FIG. 18a with a semi-deployed rotational element prolonged by two elongated arcs.

FIGS. 18a, 19 and 20a describe extended members 20a, 20b arranged for most of their length in the cavity 9.6 of the body 2.6. In a variation of this seventh embodiment, the extended members may be connected to the rotational element 12.6 and the rod 16.6, entirely within the cavity 10.6, such that no slits are required and the rotational element 12.6 with its arc components 20a, 20b may complete a 360° revolution around its medial longitudinal axis. In another variation of this seventh embodiment slits may be arranged on that portion of the superior and inferior surfaces 3.6a, 3.6b which are covering the lateral sides 7.6a, 7.6b of the body 2.6, such slits corresponding to the shape of the extended members 20a, 20b in order to receive such extended members 20a, 20b when they are not deployed.

In additional variations of this seventh embodiment, the extended members 20a, 20b may have different shapes: they may have one or several bends along their length and their length may be arranged following several different axes. FIG. 20b describes the extended members 20a and 20b arranged in parallel planes one relative to the other, but the two extended members 20a, 20b may also be arranged in non-parallel planes, such as planes converging towards the posterior part 6.6, or towards the anterior part 5.6 of the body 2.6. FIGS. 19, 20a and 20b describe the extended members 20a, 20b as a rigid ribbon, but their cross section may also be square, round, oval or ellipsoidal, oblong, ovate, triangular, rhombic, trapezoidal or polygonal with more than four sides.

FIGS. 23a to 24b describe an eighth embodiment of the invention, wherein the rotational element 12.7 of the cage 1.7 is only consisting in two symmetrically opposed connecting arcs 20.7a, 20.7b, which match the functionality of the rotational element 12.6 of the seventh embodiment. The two arcs 20.7a, 20.7b are connecting to each other at their proximal ends 21.7a, 21.7a' and at their distal ends 21.7b, 21.7b'. The proximal and distal ends 21.7a, 21.7a', 21.7b, 21.7b' are received in correspondingly shaped slits 22.7a, 22.7a', 22.7b, 22.7b' arranged respectively in the anterior part 5.7 of the body 2.7 and in the superior and inferior surfaces 3.7a, 3.7b at the posterior part 6.7 of the body 2.7, before the rotation of the rotational element 12.7 is actuated. The insertion of this cage 1.7 between two vertebrae 4a, 4b is completed according to the same method as described in FIGS. 6a to 6e for the first embodiment. As with the arcs 20a, 20b of the seventh embodiment, the arcs 20.7a, 20.7b of the cage 1.7 protect the vertebrae 4a, 4b against the abrasion of the crenellated superior and inferior surfaces 3.7a, 3.7b of the cage during the whole insertion process.

Variations of the seventh and eighth embodiments consist in arranging arcs 20a, 20.7a, 20b, 20.7b asymmetrically only on one of the superior surface 3.6a, 3.7a or inferior surface 3.6b, 3.7b of the body 2.6, 2.7. The method of insertion is similar to the one described for the third embodiment, where the rotational element 12.6, 12.7 in this variation only engages one or the other of the superior or inferior vertebrae 4a or 4b at any given time, while the other of the superior or inferior surfaces 3.6a, 3.7a or 3.6b, 3.7b of the body 2.6, 2.7 engages the other vertebra 4a or 4b.

According to a ninth embodiment of the invention, represented in FIGS. 23a to 24b, the cage 1.8 has a rotational element 12.8 comprising of two opposing arcs 20.8a, 20.8b, which do not connect in the wedge-shaped anterior part 5.8 of the body 2.8 as in the eighth embodiment, but instead, their proximal ends 21.8a, 21.8b connect together at the level of the anterior inner-side 10.8a of the cavity 9.8. These arcs 20.8a, 20.8b are not configured to significantly distract the intervertebral space by their rotation, but rather to shield the vertebrae 4a, 4b against the abrasion of the crenellated superior and inferior surfaces 3.8a, 3.8b of the cage 1.8 during the introduction of the cage 1.8. In this eighth embodiment, the arcs 20.8a, 20.8b are deployed already before the insertion of the anterior part 5.8 of the body 2.8, and there is no rotation needed (corresponding to the step described in FIG. 6b for the first embodiment). The method of insertion is to fully introduce the cage 1.8 with the pre-deployed arcs 20.8a, 20.8b between the two vertebrae 4a, 4b, similar to what is shown in FIG. 6c for the first embodiment, until the cage 1.8 has reached its final position. The rotational element 12.8 is then rotated between 60° and 90°, in order to collapse the arcs 20.8a, 20.8b in the cavity 9.8 below the level of the superior and inferior surfaces 3.8a, 3.8b, similar to the step described in FIG. 6d for the first embodiment: The last step is to remove the rod 16.8 as described in FIG. 6e.

Figure 25A:
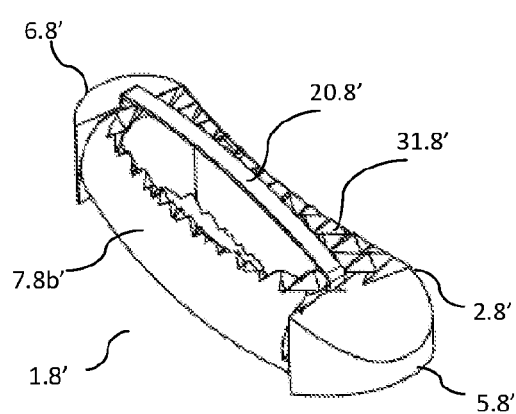
FIG. 25a represents a perspective view of a variation of the ninth embodiment with a crescent-shaped cage and fully deployed shielding component in the shape of one single arc.
Figure 25B:
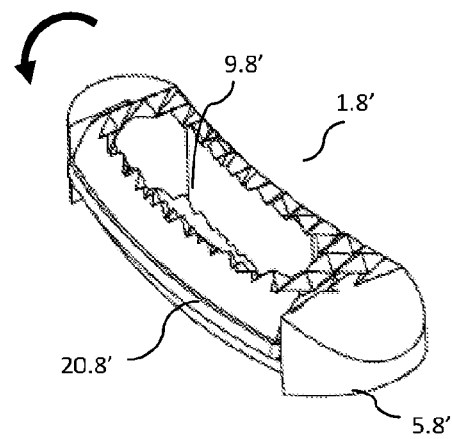
FIG. 25b represents a perspective view of the same crescent-shaped cage as in FIG. 25a but with a collapsed shielding component in the shape of a single arc.
Figure 28:
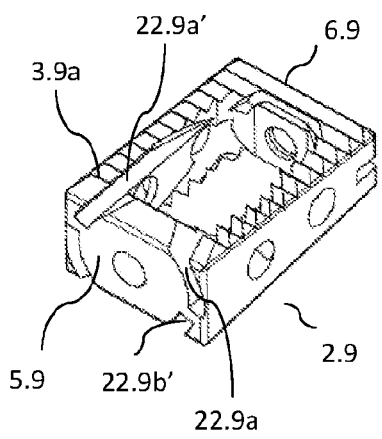
FIG. 28 represents a perspective view of the body of the cage of the tenth embodiment.

FIGS. 25a and 25b represent a first variation of the ninth embodiment, where the cage 1.8' has an elongated crescent-shaped body 2.8', as in the third embodiment, but with a non-mobile anterior part 5.8', unlike in the third embodiment. The rotational element 12.8 only features one arc 20.8', which has a curved shape corresponding to the curvature of the lateral side 7.8b' of the body 2.8'. During the insertion process for the cage 1.8', the arc 20.8' only shields the superior vertebra 4a, from the crenellated superior surface 3.8a' of the body 2.8'. Another difference with the cage 1.8 is shown in FIG. 25b, where the arc 20.8' collapses laterally beyond the lateral side 7.8b' of the body 2.8'.

FIGS. 26a, 26b and 26c represent another variation of the ninth embodiment, where the cage 1.8" has the same body 2.8' as the one of the cage 1.8' in the previous variation, but the rotational element 12.8" comprises a rotund shield 20.8" in lieu of an arc. This shield 20.8" increases the protection surface of the vertebra against the abrasion of the crenellated surface 31.8a of the superior surface 3.8a. In addition, as described in FIGS. 26b and 26c, once the shield 20.8" is collapsed after the lateral rotation, if the width of the shield 20.8" is larger than the distance H between the superior and inferior surfaces 3.8a', 3.8b' of the body 2.8', such lateral edges of the shield 20.8" engage the endplates of the vertebrae 4a, 4b and may serve as a ridge to impose a curved trajectory "T' to the cage 1.8", when said cage is pushed forward by directional force "F" into the intervertebral space. In addition, such configuration of the shield 20.8" may also serve as an anchoring feature for the cage 1.8".

In a further variation of cages 1.8' and 1.8", the arc 20.8' or shield 20.8", instead of being arranged to collapse beyond the lateral side 7.8b' of the body 2.8', as described in FIGS. 25b, 26b and 26c, the arc 20.8' or shield 20.8" may also be arranged so as to collapse into a longitudinal slit arranged in the superior and inferior surfaces 3.8a', 3.8b' of the body 2.8', such cavity allowing the full or partial lodging of the arc 20.8' or shield 20.8". If the collapsed arc 20.8' or shield 20.8" are arranged so that their sides protrude beyond the crenellated surfaces 31.8 of the body 2.8, then, they may provide the same steering function as for the cage 1.8" shown in FIG. 26c.

According to another variation of the ninth embodiment, a cage 1.8, 1.8', 1.8" may be arranged with two opposing arcs 20.8a, 20.8b, 20.8a', 20.8b' or shields 20.8a", 20.8b", arranged symmetrically such that each covers respectively one of the superior and inferior surfaces 3.8a, 3.8b, 3.8a', 3.8b' of the body 2.8, 2.8', 2.8" and each to collapse, after a lateral rotation of the shields rotational elements 12.8', 12.8".

FIG. 27a describes yet another variation of a cage of the ninth embodiment, wherein the cage 1.8'" has an arc 20.8'" comprising, on a portion of its outward facing side, a longitudinal curved ridge 23, which is arranged to offer a suitable profile (as shown in FIG. 27b) to engage the vertebrae 4a and thereby cause a thin carving in its endplate and steer a different trajectory "T" to the directional force "F" actuated on the posterior part 6.8' of the body 2.8' of the cage 1.8'", similar to mechanism of the collapsed shield 20.8" described in FIG. 26c. In additional variations, the ridge 23 may also be straight instead of curved, and may have a different cross-section, such as be arranged with two edges along its longitudinal axis with a cross-section of a square, a rectangle or trapezoidal shaped. The ridge 23 may also be arranged on a cage 1.8 with arcs 20.8a, 20.8b or on a cage 1.8" with a shield 20.8" such as the ones shown in FIG. 23a or 26a. In additional variations, the shapes, lengths and profiles of the ridge may also vary between the distal part 21.8a'" and proximal part 21.8b'" of the arc 20.8a, 20.8b, 20.8' or shield 20.8".

Cages 1.7, 1.8, 1.8', 1.8", 1.8'" of the ninth embodiment may also be arranged with rotational members 12.8, arcs 20.8a, 20.8b and shields 20.8" which are removable from the implant.

A tenth embodiment of the invention, described in FIGS. 28 to 30d, combines a rotational element 12.9 similar to the rotational element 12.7 of the eighth embodiment, with a body 2.9 with a flat anterior part 5.9. The body 2.9 represented in FIG. 28 has slits 22.9a, 22.a', 22.9b, 22.9b' capable of receiving the arcs 20.9a, 20.9.b in two of their multiple configurations.

Figure 29:
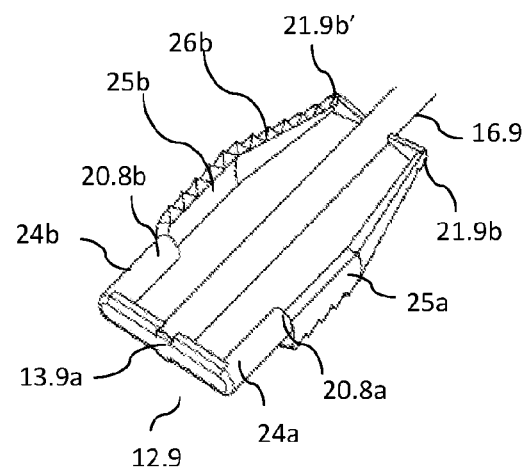
FIG. 29 represents a perspective view of the rotational element with crenellated arcs of the cage of the tenth embodiment.

FIG. 29 describes the rotational element 12.9 with two symmetrically opposed arcs 20.9a, 20.9b, each having a first portion at their proximal end 21.9a, 21.9b in the shape of insertion rods 24a, 24b and a second portion as extended members 25a, 25b, ranging until the distal end 21.9a', 21.9b' of the arcs 20.9a, 20.9b. The extended members 25a, 25b have three smooth sides and one crenellated side 26a, 26b. The insertion rods 24a, 24b are connected together with a connecting member 13.9a serving as anterior side of the rotational element 12.9. The two insertion rods 24a, 24b define, with their two respective lateral sides, two parallel virtual planes corresponding to superior and inferior surfaces 15.9a, 15.9b of the rotational element 12.9. The outer facing side of each of the insertion rods 24a, 24b define the lateral sides 14.9a, 15.9b of the rotational element 12.9, and the distance between them defining the long dimension D. The two sets of two perpendicular planes together define a virtual flattened rectangle, the function of which is to be easily introduced between two slightly distracted adjacent vertebrae 4a, 4b.

Figure 30A:
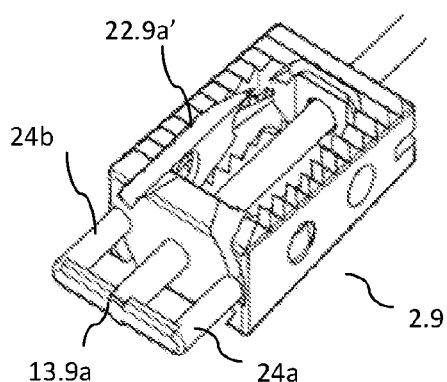
FIG. 30a represents a perspective view of the cage of the tenth embodiment with a rotational element with crenellated arcs in a first configuration.
Figure 30B:
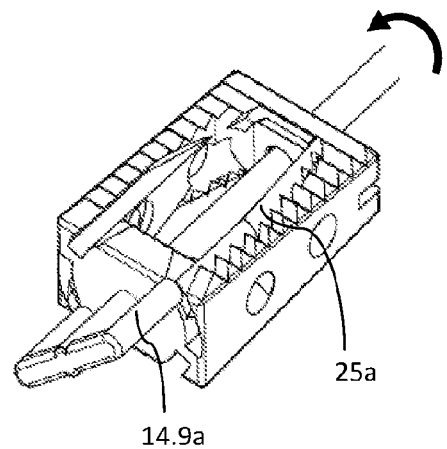
FIG. 30b represents a perspective view of the cage of the tenth embodiment in a second configuration after a rotation.

The purpose of the extended members 25a, 25b, is dual: in the configuration of the rotational element 12.9 shown in FIG. 30b, with one smooth side protruding from the superior and inferior surfaces 3.9a, 3.9b, the extended members 25a, 25b are shielding the vertebrae 4a, 4b from the abrasion of the crenellated superior and inferior surfaces 3.9a, 3.9b of the body 2.9. In the configuration of the rotational element 12.9 shown in FIG. 30d, the crenellated sides 26a, 26b of the extended members 25a, 25b contribute to the anchoring of the cage 1.9 into the adjoining vertebrae 4a, 4b.

Figure 30C:
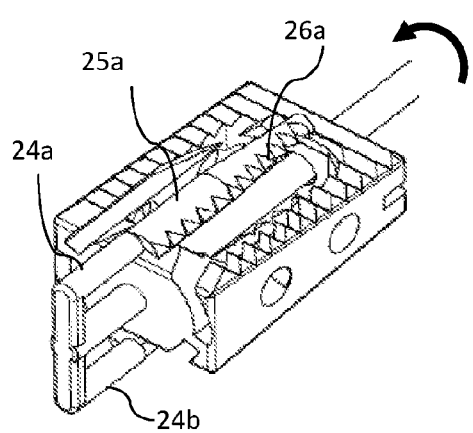
FIG. 30c represents a perspective view of the cage of the tenth embodiment in a third configuration with a rotational element with crenellated arcs in the course of being rotated.
Figure 30D:
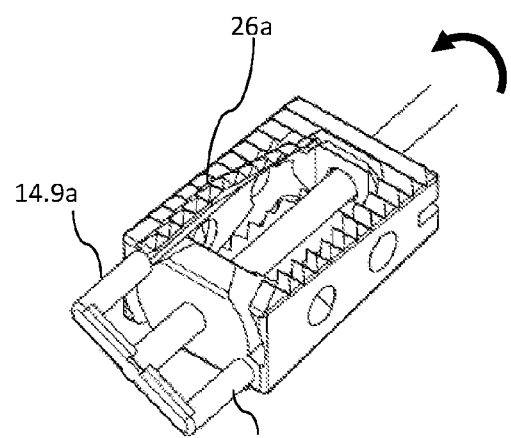
FIG. 30d represents a perspective view of the cage of the tenth embodiment with a rotational element with crenellated arcs in its final configuration after its rotation.

The insertion of the cage 1.9 proceeds a follows: FIG. 30a describes the configuration, where the anterior side 13.9a of the rotational element 12.9 and the opposing insertion rods 24a, 24b are first introduced between slightly distracted vertebrae 4a, 4b. As shown in FIG. 30b, the rotational element 12.9 is then rotated approximately 45° which causes the two virtual planes 15.9a, 15.9b of the insertion rods 24a, 24b to engage the vertebrae and to distract them, and the smooth side of the extended members 25a, 25b situated opposite to the crenelated side 26a, 26b, to protrude from the crenellations of the superior and inferior surfaces 3.9a, 3.9b of the body 2.9, thus creating a smooth rail shielding the adjoining vertebrae from the abrasion of the crenellated body 2.9 of the cage 1.9 while the cage is pushed into the interbody space. Once the body 2.9 is introduced, the rotational element 12.9 may be rotated further for another 45° (as shown in FIG. 30c), until the smooth sides of the extended members 25a, 25b opposite to the crenelated side 26a, 26b rest at the bottom of the rims 22.9a' 22.9b' of the body 2.9, as shown in the configuration of FIG. 30d. The total rotation of the rotational element 12.9 between FIG. 30a and FIG. 30d is in a range between 150° and 170°. The crenellated sides 26a, 26b of the extended members 25a, 25b are protruding from the superior and inferior surfaces 3.9a, 3.9b of the body 2.9 and may also increase the height of the cage 1.9.

The extended members 25a, 25b may also be arranged with a rod 16.9 that engages only the distal ends 21.9b, 21.9b' of said extended members 25a, 25b, thus avoiding the need for the rod 16 to cross the cavity 9 of the body 2.9 and to engage the rotational element 12.9 at the proximal ends 21.9a, 29a' of the extended members 25a, 25b. This variation is also relevant for the engagement of the arcs 20a, 20b of the cages of the seventh to ninth embodiments and their variations.

In FIGS. 28 to 30d, the extended members 25a, 25b are not parallel to each other, but in a variation of the tenth embodiment, they may be arranged in parallel axes to each other or to converge towards the anterior part 5.9 of the body 2.9, instead of towards its posterior part 6.9.

In the same FIGS. 28 to 30d, the anterior section of the rotational element 12.9 with the insertion rods 24a, 24b is configured in the same plane as the extended members 25a, 25b. In a variation of the tenth embodiment, the plane defined the opposing insertion rods 24a, 24b may be angled relative to the plane defined by the extended members 25a, 25b with the two planes having a center of rotation on the medial longitudinal axis of the cage 1.9. The advantage of such variation is that the crenellated sides 26a, 26b of the extended members 25a, 25b, as they anchor into the respective vertebrae 4a, 4b, may stabilize the insertion rods 24a, 24b in a deployed configuration and maintain their outer-facing sides 14.9a, 14.9b engaged with the two vertebrae 4a, 4b.

Figure 31A:
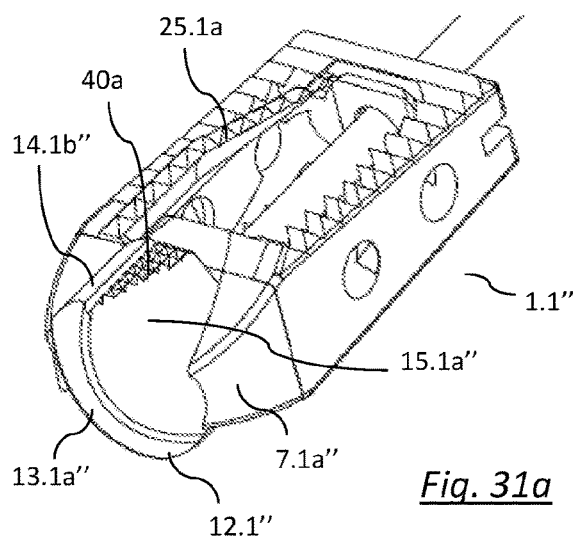
FIG. 31a represents a perspective view of a variation of the cage of the tenth embodiment with a rotational element with a wedge-shaped tip and crenellated arcs in its final configuration after its rotation.
Figure 31B:
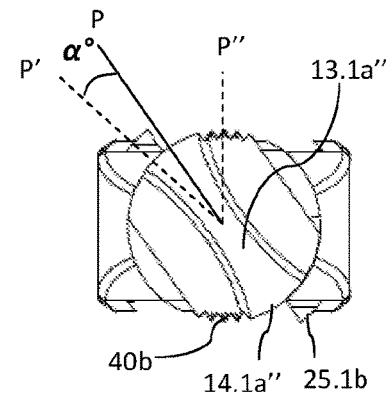
Figure 31C:
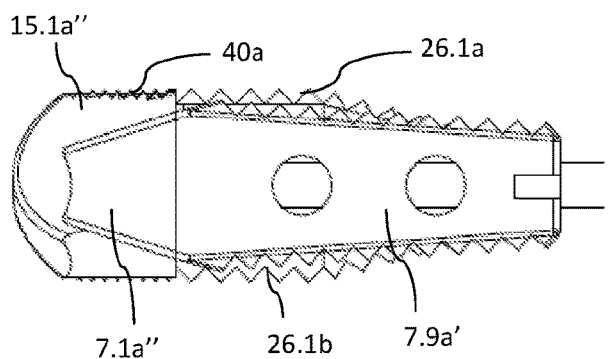
FIG. 31c represents a lateral view of the cage in the same configuration as in FIGS. 31a and 31b.

FIGS. 31a, 31b and 31c describe a variation of the foregoing variation, wherein the insertion rods 24a, 24b configuration is replaced with a wedge-shaped rotational element 12.1" similar to wedge-shaped rotational element 12.1' of the second embodiment, and the body 2.1" has two flanks 7.1a", 7.1b" protecting the crenellated surfaces 40a, 40b on the lateral sides 14.1a", 14.1b" of the rotational element 12.1". As for the other variations of the tenth embodiment, the first benefit of this variation is that the smooth side of the extended members 25.1a, 25.1b arranged opposite to the crenellated sides 26.1a, 26.2 serve as gliding lane when the cage 1.1" is introduced between two vertebrae 4a, 4b (similar to the configuration shown in FIG. 30b).

The second benefit of this variation, is to extend the load bearing surface of the cage 1.1" relative to the vertebrae 4a, 4b. FIG. 31b describes plane P cutting across the two lateral sides 14.1a", 14.1b" on their highest separation line, which defines the long dimension D for the introduction of the cage 1.10 in the interbody space. A second plane P' cuts across the opposing crenellated sides 26.1a, 26.1b of the extended members 25.1a, 25.1b on their highest separation point, while a third plane, P'", cuts across the highest point of the respective crenellated surfaces 40a, 40b arranged on a portion of the lateral sides 14.1a" and 14.1b". In the final configuration of the cage 1.1" shown in FIG. 31b, plane P'" is arranged perpendicular to the endplates of the vertebrae 4a, 4b. Planes P and P' are arranged at an angle α of approx. 12° and plane P' and P'" at an angle of 48° relative to one another. Thanks to that angle between planes P' and P'", the load bearing surface of the rotational element 12.1" defined by the crenellated extended members 25.1a, 25.1b and the crenellated surfaces 40a, 40b of the lateral sides 14.1a", 14.1b" of the wedge-shaped tip of the rotational element 12.1", is greatly widened and the position of the rotational element 12.1", is secured against tilting. As shown in FIG. 31c, the durably deployed rotational element 12.1" has also the benefit of increasing the load bearing length of the cage 1.11" against the adjoining vertebrae. In a variation, the crenellated surfaces 40a, 40b of the lateral sides 14.1a", 14.1b" may also be arranged in planes converging towards the posterior side 13.1b" of the rotational element 12.1", in order to match the angled gradient of the lordotic superior and inferior surfaces 3.1a", 3.1b" of the body 2.1" and allow for an extended planar load bearing surface to the cage 1.1".

Figure 32A:
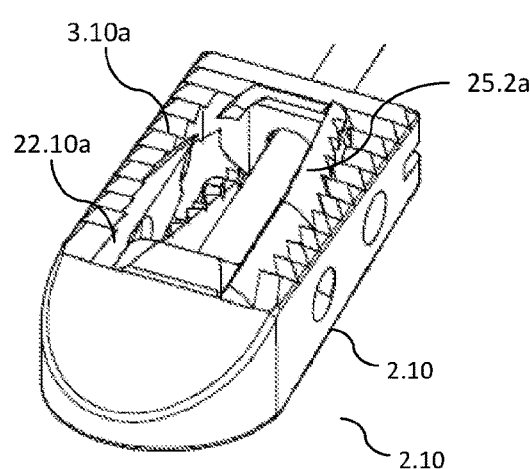
FIG. 32a represents a perspective view of a cage with a body having a wedge-shaped tip of the eleventh embodiment with a non-deployed rotational element in the shape of crenellated arcs.
Figure 32B:
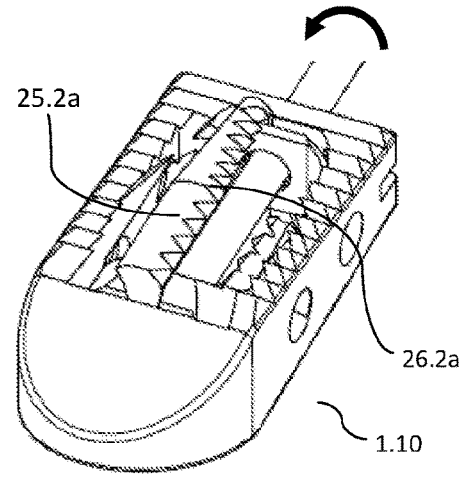
FIG. 32b represents a perspective view of the same cage as in FIG. 32a but with its rotational element shown during deployment.
Figure 33:
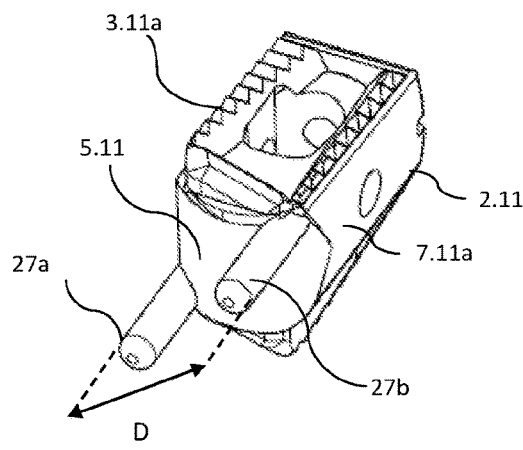
FIG. 33 represents a perspective view of the diamond-shaped body of a cage of the twelfth embodiment with two parallel insertion rods.
Figure 34:
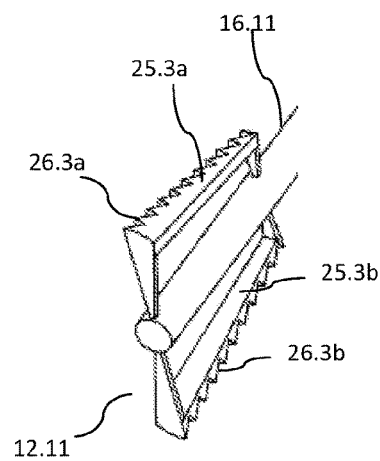
FIG. 34 represents a perspective view of the rotational element of the cage of the twelfth embodiment with two crenellated arcs.

FIGS. 32a and 32b describe the eleventh embodiment of a cage 1.10 with extended members 25.2a, 25.2b with crenellated sides 26.2a, 26.2b, arranged in a body 2.10 with a wedge-shaped anterior part 5.10, in order for cage 1.10 to benefit of the advantages described for the cage 1.9 of the tenth embodiment. The rotational element 12.10 of the eleventh embodiment is similar to the rotational element 12.11 shown in FIG. 34 for the twelfth embodiment. The cage 1.10 is introduced into the interbody space as described in FIG. 6a, with the smooth side of the extended members 25.2a, 25.2b protruding from the crenellated superior and inferior surfaces 3.10a, 3.10b of the body of the cage 1.10, as in the configuration of FIG. 32a, to shield the vertebrae 4a, 4b from the abrasion of the crenelated superior and inferior surfaces 3.10a, 3.10b. The cage is then pushed until its final position, where the rotational element 12.10 is rotated, actuating a distraction of the vertebrae 4a, 4b by the pressure of the outward facing smooth side of the extended members 25.2a, 25.2b in the configuration shown in FIG. 32b. The rotational element is then further rotated until the smooth side opposite to the respective crenellated sides 26.2a, 26.2b rests at the bottom of the rims 22.10a', 22.10b' and the crenellated sides 26.2a, 26.2b engage the vertebrae 4a, 4b.

A variation of this cage 1.10 of the eleventh embodiment consists in arranging a rotational element 12.10 with two sets of two opposing extended members 25.2a, 25.2b which together define the external structure of a slightly flattened rectangular shape, which, when rotated, may expand the cage 1.10 to increase the space between the adjoining vertebrae.

According to FIGS. 33 to 37f, a twelfth embodiment of the invention is described, wherein a cage 1.11 comprises a rotational element 12.11 similar to the rotational element 12.10 of the eleventh embodiment, and a body 2.11 which, has a tip arranged on its anterior part 5.11, in the shape of two opposing fixed rods 27a, 27b positioned obliquely in two opposing corners of the anterior side 5.11 of the body 12.11. The fixed rods 27a, 27b of the body 12.11 define, with their respective outer-facing sides and their two respective lateral sides, a virtual flattened rectangle similar to the virtual rectangle defined by the rods 24a, 24b of the rotational element 12.9 of the tenth embodiment. The body 2.11 has an essentially diamond shaped cross-section, where the overall plane of the superior surface 3.11a has an obtuse angle relative to the overall plane of one lateral side 7.11a and has an acute angle relative to the overall plane of the other lateral side 7.11b, while conversely, the inferior surface 3.11b has an obtuse angle relative to the lateral side 7.11b and an acute angle with the other lateral side 7.11a of the body 2.11. In variations of this eleventh embodiment, the obtuse and acute angles of the edges of the superior and inferior surfaces 3.11a, 3.11b do not need to be constant along the full the length of the superior and inferior surfaces 3.11a, 3.11b from the anterior part 5.11 to the posterior part 6.11 of the body 2.11, and the cross-section of the body may even not have a diamond-shape along the whole length of the body 2.11, but a rectangular or trapezoidal shape on one or more portions of it.

Figure 35A:
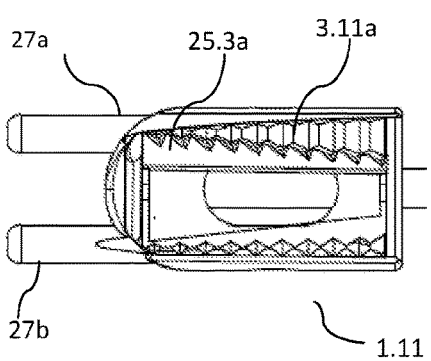
FIG. 35a represents a top down view of the diamond-shaped cage of the twelfth embodiment with a non-deployed rotational element.
Figure 35B:
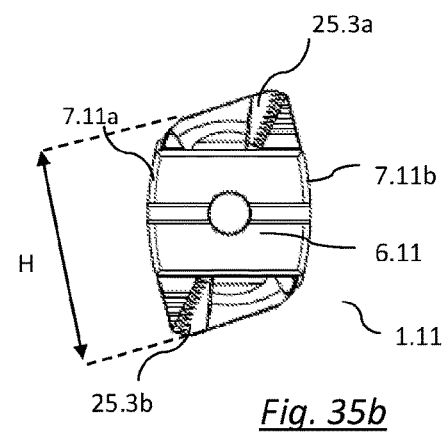
FIG. 35b represents a back view of the same cage as in FIG. 35a with the rotational element in the same configuration.
Figure 36A:
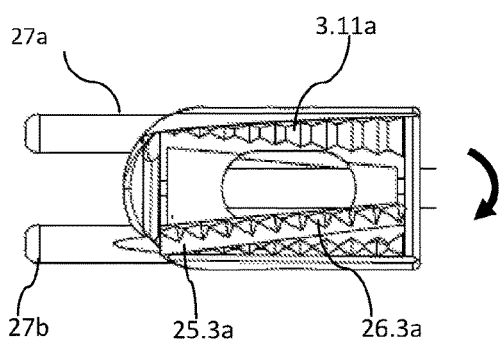
FIG. 36a represents a top down view of the diamond-shaped cage of the twelfth embodiment with a deployed rotational element.
Figure 36B:
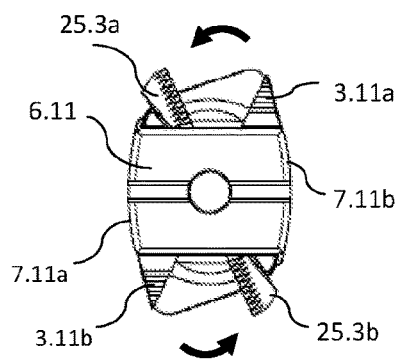
FIG. 36b represents a back view of the same cage as in FIG. 36a with the rotational element in the same configuration.

The benefit of this twelfth embodiment is to introduce cages 1.11 with higher lordotic angles between two vertebrae through two contributing factors. The first factor is that, the distance (at a perpendicular angle) between the superior and inferior surfaces 3.11a, 3.11b on the anterior part 5.11 of the body 2.11, which ultimately defines the distance H (as shown in FIG. 35b) between the vertebrae 4a, 4b when the cage 1.11 is finally positioned between two vertebrae, is only marginally smaller than the distance between the outer-facing side of each of the opposing fixed rods 27a, 27b which define height H1, but exceeds the distance between the superior and inferior surfaces of a body arranged with similar opposing rods but which has an essentially square or rectangular cross section as described in the referenced prior art. With a higher distance on the anterior part 5.11 of this body 2.11, but with a same height of the posterior part 6.11, the angulation between the anterior part 5.11 and the posterior part 6.11 of the body 2.11 may be increased. The second contributing factor is that the diamond shaped body 2.11 is suitable to receive the extended members 25.3a, 25.3b of the rotational element 12.11 in a first configuration, with one of their smooth sides protruding, as described in FIGS. 35a, 35b during the first insertion steps (shown in FIGS. 37a to 37c) and to receive the extended members 25.3a, 25.3b with their crenellated sides 26.3a, 26.3b protruding, in a second configuration after rotation of the rotational element 12.11, as described in FIGS. 36a, 36b, in the last step of the insertion shown in FIG. 37f.

Figure 37A:
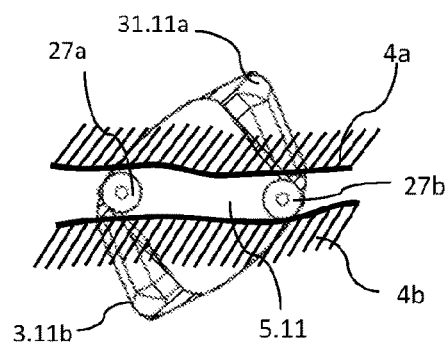
FIG. 37a represents a front view of the diamond-shaped cage of the twelfth embodiment with its insertion tips engaged between two schematic vertebrae in a first configuration with a non-deployed rotational element.
Figure 37B:
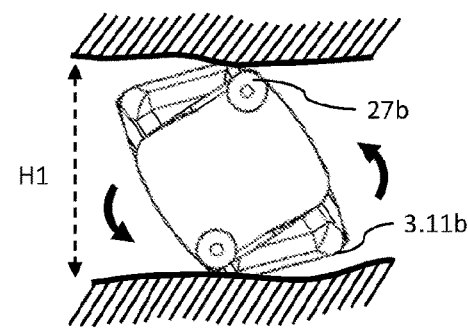
FIG. 37b represents the same cage as in FIG. 37a but with distracted schematic vertebrae after a rotation of the body of the cage in a second configuration.
Figure 37C:
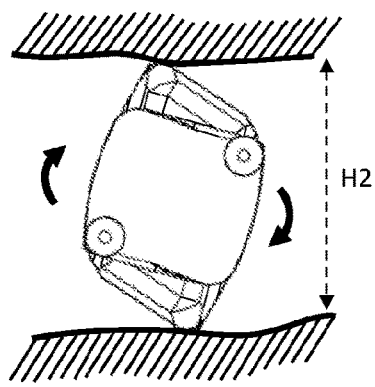
FIG. 37c represents the same cage as in FIGS. 37a and 37b but with further distracted schematic vertebrae after a counter rotation of the body of the cage in a third configuration.
Figure 37D:
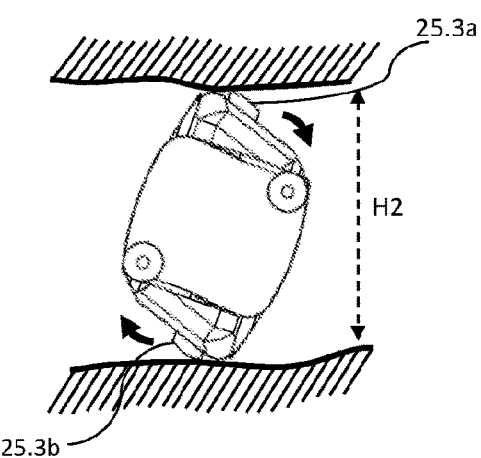
FIG. 37d represents the same cage as in FIGS. 37a to 37c with the body in the same position as in FIG. 37c and with a deploying rotational element actuated by rotation.
Figure 37E:
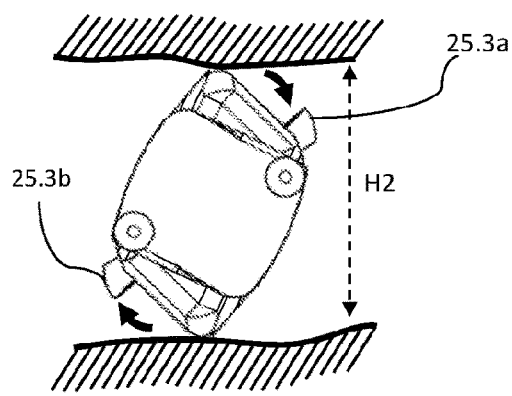
FIG. 37e represents the same cage as in FIGS. 37a to 37d with the body in the same position as in FIGS. 37c and 37d but with a deployed rotational element in a fourth configuration.
Figure 37F:
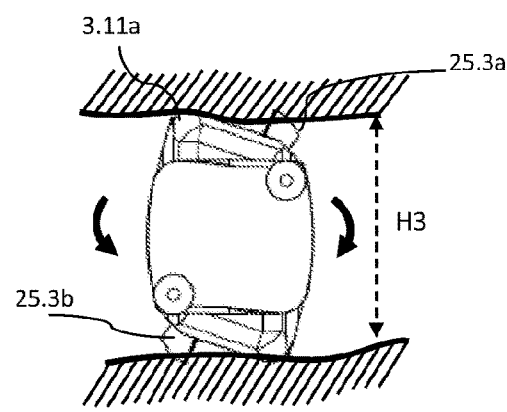
FIG. 37f represents the same cage as in FIGS. 37a to 37e with the body in a final configuration with a deployed rotational element.

The mechanism of insertion of the cage 1.11 into the intervertebral space is described in FIGS. 37a to 37f. According to FIG. 37a, the opposing fixed rods 27a, 27b are first introduced between the collapsed vertebrae 4a, 4b, with the long planes defined by the outer facing sides of the fixed rods 27a, 27b being essentially parallel to the endplates of the vertebrae 4a, 4b. The cage 1.11 is pushed until the anterior part 5.11 of the body 2.11 is in contact with the vertebrae 4a, 4b. The cage 1.11 is then rotated approximately 85° as shown in FIG. 37b. That rotation angle may go up to 90° or may be lower, such as between 70° and 85°, depending on the steepness of the gradient of the superior and inferior surfaces 3.6a, 3.6b defined by their obtuse and acute angles with the lateral sides 7.11a 7.11b. The outer facing sides of the two fixed rods 27a, 27b define height H1 and separate the vertebrae 4a, 4b of that distance. The cage 1.11 is then pushed forward gliding on two of its oblique opposing edges to its final location. FIG. 37c describes the cage in its final position within the interbody space, but still not in its final configuration, after it has been rotated in the opposite direction to the direction in the step in FIG. 37b, approximately of an angle of 50°: the height H2 defined by the opposing acute angled edges of the body 2.11 is superior to heights H and H1. According to FIGS. 37d and 37e, the extended members 25.3a, 25.3b are then deployed by a lateral rotation of the rotational element 12.11 of an angle of approximately 50°. In the final configuration, described in FIG. 37f, the crenellated sides 26.3a, 26.3b of the extended members 25.3a, 25.3b and the crenellations 31.11a, 31.11b on the opposing side of the superior and inferior surfaces 3.11a, 3.11b of the body 2.11, which together now define the plane of essentially flat superior and inferior surfaces 3.11a, 3.11b of the body 2.11, engage the vertebrae 4a, 4b and anchor into the endplates. The height H3 on the highest section of distraction of the vertebrae is now height H3, which is smaller than height H2 but longer than H1. The cage 1.11 and the rotational element 12.11 are pushed and rotated by means of a removable rod 16.11, or of any other technically suited instrument, which is then removed.

Figure 38A:
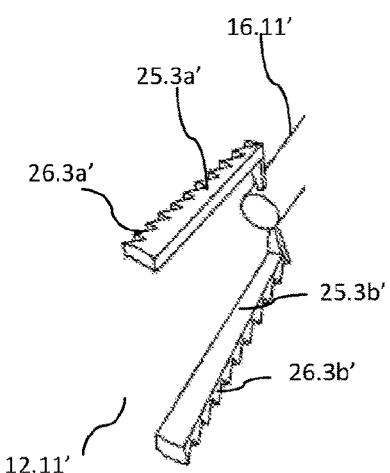
FIG. 38a represents a variation of the rotational element of FIG. 34.
Figure 38B:
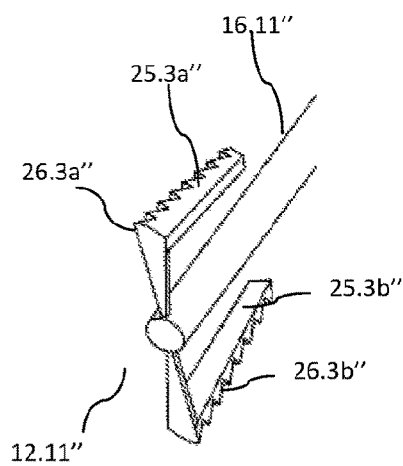
FIG. 38b represents another variation of the rotational element of FIG. 34.

In variations of the twelfth embodiment, the fixed rods 27a, 27b may also be arranged as mobile components which are retractable into the body 12.11 or fully removable from the cage 1.11. In two additional variations described in FIGS. 38a and 38b, the elongated members 25.3a', 25.3b', 25.3a", 25.3b" of the rotational element 12.11', 12.11" may be arranged as U shaped constructs connected only at one of the proximal or distal ends to the delivery rod 16.11', 16.11". The U shaped rotational element 12.11', 12.11" may also be connected to the body 2.11', 2.11" on the outer surface of the posterior part 6.11' of the body 2.11' in the case of the rotational element 12.1' of FIG. 38a, or on the outer surface of the anterior part 5.11", of the body 2.11" in the case of the rotational element 12.1" of FIG. 38b. This may be more practical for the assembly of the body 2.11', 2.11" and the rotational element 12.11', 12.11" of the cage 1.11', 1.11".

Figure 39A:
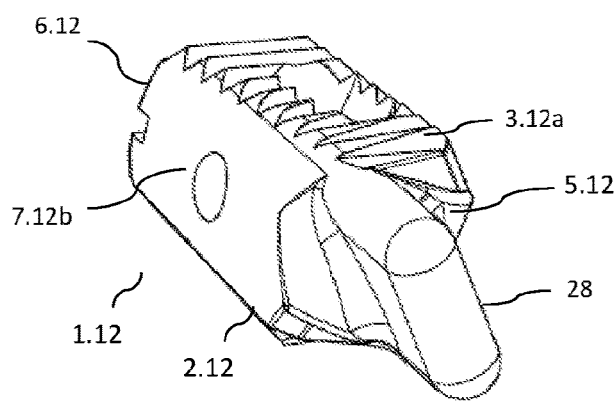
FIG. 39a represents a perspective view of a diamond-shaped cage with full insertion tip and without rotational element.
Figure 39B:
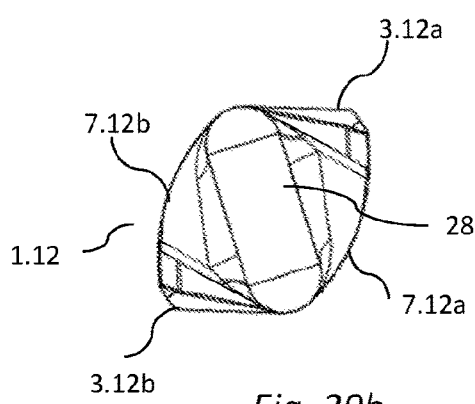
Figure 39C:
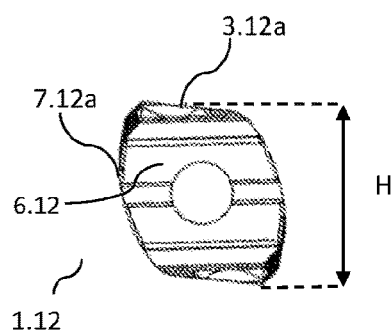

In another variation of the twelfth embodiment, the virtual flattened rectangle defined by the sides of the fixed rods 27a, 27b of cage 1.11, may be arranged as full flat insertion tip 28 of a cage 1.12, as shown in FIGS. 39a to 39c. The tip 28 of the body 2.12 serves the same purpose as the flattened rectangle defined by fixed rods 27a, 27b of the body 2.11.

Figure 40A:
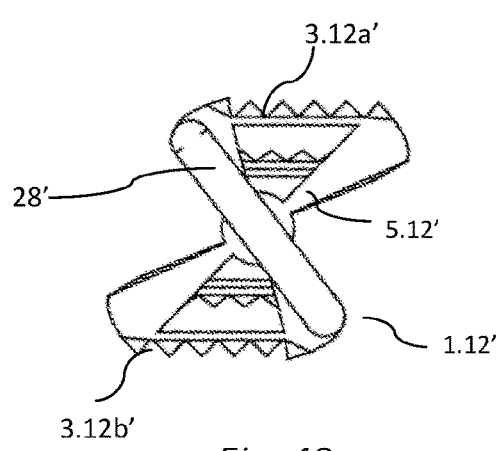
FIG. 40a represents a front view of a diamond-shaped skeleton cage with closed insertion tip and without rotational element.
Figure 40B:
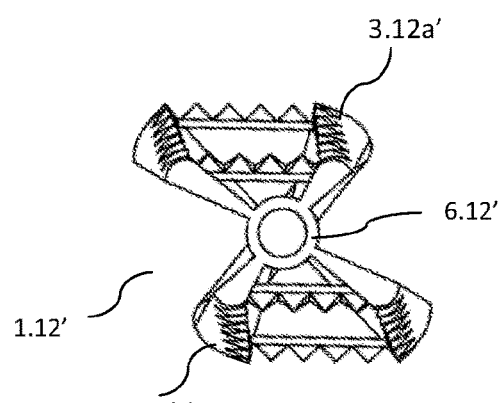
Figure 40C:
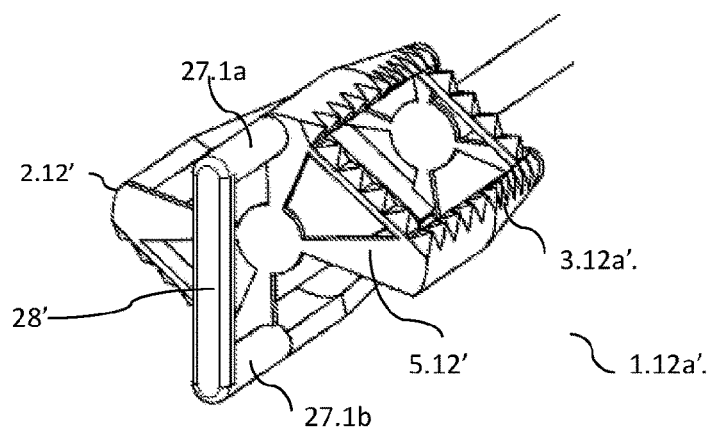

FIGS. 40a to 40c represent a similar variation of a cage 1.12' where the diamond-shaped body 2.12' is reduced to a skeleton defining the outer volumes of the diamond-shaped body 2.12' and the tip 28' has its outer volume defined by diagonally arranged parallel fixed rods 27.1a, 27.1b connected together at their distal part by a connecting plate similar to plate 13.9a of the tenth embodiment. Both diamond-shaped bodies 2.12 and 2.12' of these variations may be arranged so as to be capable to receive a rotational elements 12.11, 12.11', 12.11" such as those described in FIGS. 34, 38a and 38b. The diamond-shaped bodies 2.11, 2.12 and 2.12" of the twelfth embodiment and of its variations may also be used as stand-alone cages without rotational element, to achieve the distraction of the vertebrae 4a, 4b up to a height H, which is an intermediate step to those described in the steps of FIGS. 37b and 37c.

Figure 41A:
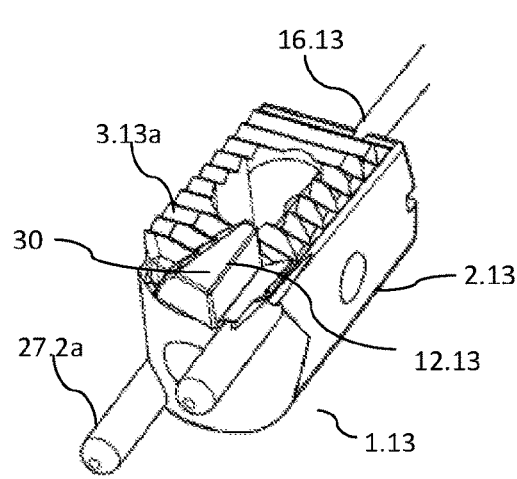
FIG. 41a represents a perspective view of the asymmetrical cage of the thirteenth embodiment with an ex-centered non-deployed rotational element.
Figure 41B:
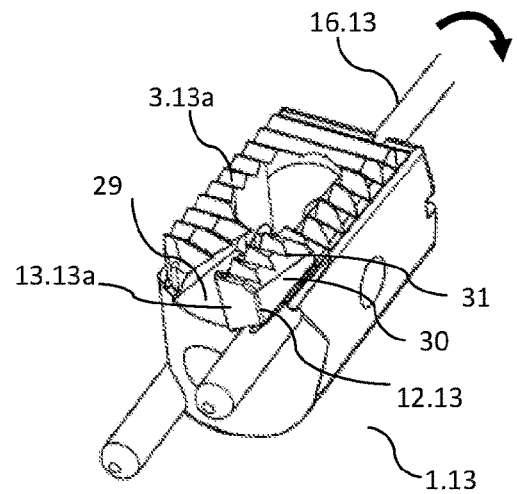
FIG. 41b represents a perspective view of the same asymmetrical cage as in FIG. 41a but with deployed ex-centered rotational element.

FIGS. 41a and 41b describe a thirteenth embodiment of the invention with a cage 1.13 comprising a body 2.13 which has asymmetric superior and inferior surfaces 3.13a, 3.13b and an expansion element 12.13 designed to be deployed only beyond the superior surface 3.13a of the body 2.13.

Figure 42:
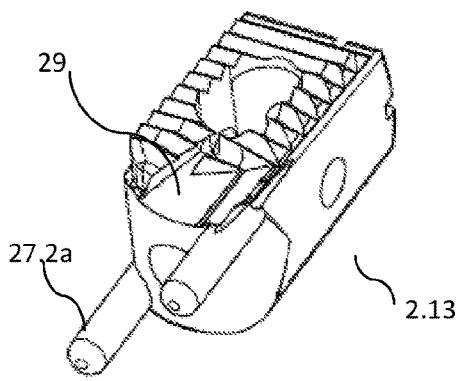
FIG. 42 represents the body of the asymmetrical cage of the thirteenth embodiment.
Figure 44A:
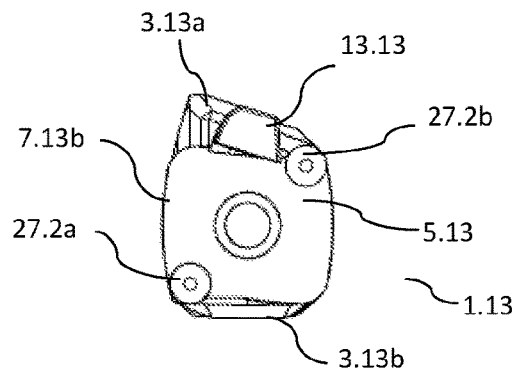
FIG. 44a represents a front view of the same asymmetrical cage of the thirteenth embodiment as in FIG. 41a with a non-deployed rotational element.
Figure 45A:
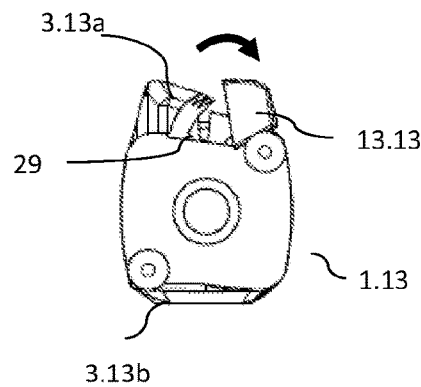
FIG. 45a represents a front view of the same asymmetrical cage of the thirteenth embodiment as in FIG. 41b with a deployed rotational element.
Figure 44B:
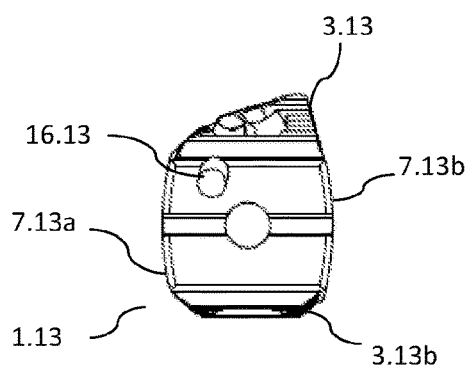
Figure 45B:
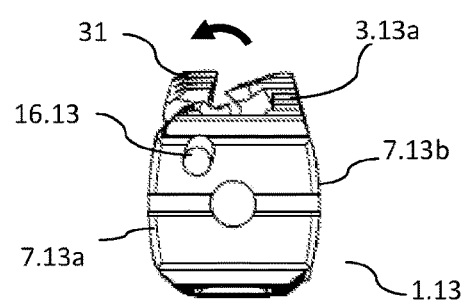
Figure 46:
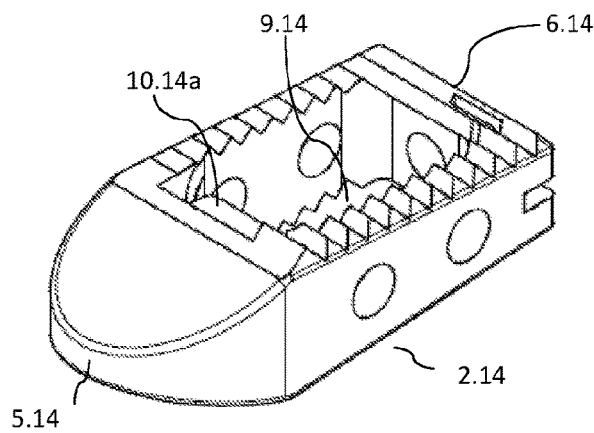
FIG. 46 represents a perspective view of the body of the symmetric cage of the fourteenth embodiment without rotational element.

According to FIGS. 42 and 44a and 45a, the body 2.13 has fixed rods 27.2a, 27.2b similar to those rods 27a, 27b of the twelfth embodiment. According to FIGS. 44b and 45b, the body 2.13 has an inferior surface 3.13b which is essentially planar and a superior surface 3.13a which is not planar. In addition, the superior surface 3.13a has one surface-portion 29 which is not crenellated and serves as receiving surface for a non-deployed rotational element 12.13. The posterior part 6.13 of the body 2.13 has an ex-centered bore 60.1 to allow the engagement of a rotation rod 16.13, which connects with the posterior side 13.13b of the rotational element 12.13.

Figure 43:
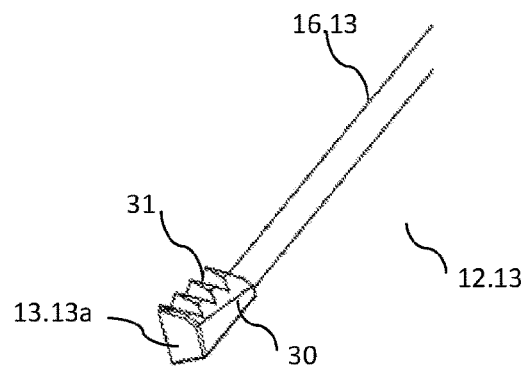
FIG. 43 represents the rotational element of the cage of the thirteenth embodiment.

As described in FIG. 43, the rotational element 12.13 has three smooth lateral surfaces, one crenellated lateral surface 31, one anterior side 13.13a and one posterior side 13.13b to engage with the rod 16.13. According to FIGS. 41a, 41.b and 44a to 45b, the rotational element 12.13 is ex-centered from the central longitudinal axis of body 2.13 both in the vertical plane and in the horizontal plane.

As shown in FIGS. 41a, 41.b and 44a to 45b, the rotational element 12.13 has two configurations: in the first configuration shown in FIGS. 41a, 44a, 44a and 41a, the rotational element 12.13 is collapsed on the surface-portion 29 of the body 2.13 and is arranged such that its smooth surface 30 is facing towards the superior vertebrae 4a. This is the configuration of the cage 1.13 during the initial steps of its insertion. The second configuration is described in FIGS. 41b, 45a and 45b: the rotational element 12.13 has been rotated laterally by means of the rotation rod 16.13 of an angle between 45° and 90°, depending on the configuration of the cage 1.13, and the smooth surface 30 is now in a parallel plane to the lateral side 7.13a of the body 2.13. The crenellated surface 31 of the rotational element 12.13 and the crenellated superior surface 3.13a of the body 2.13 now define together a relatively planar superior surface of the cage 1.13 capable of engaging the superior vertebrae 4a, anchoring into its endplate and of sharing the load relatively homogenously. Accordingly, the advantage of the invention is that while the superior and inferior surfaces 3.13a, 3.13b of the body 2.13 are asymmetrical and not entirely planar in a first configuration to allow an easy insertion, this is corrected in the final configuration by the deployed rotational element 12.13 after its rotation by actuating the rod 16.13. In addition, the deployment of the rotational element achieves the objective of increasing the height of the cage 1.13 at its anterior part 5.13.

The method of insertion of the cage 1.13 is similar to the steps described for the twelfth embodiment in FIGS. 37*a* to 37*f* but reduced to the deployment of the rotational element 12.13 only beyond one of the surfaces 3.13*a* of the body 2.13.

The rotation rod 16.13 may remain in the cage 1.13 after its actuation of the rotational element 12.13 or may be removed.

In a variation of the thirteen's embodiment, a second rotational element 12.13' may be arranged symmetrically also on the inferior surface 3.13*b* of the cage 1.13' with a surface portion 29' arranged on the inferior surface 3.13*b* to receive the rotational element 12.13'. This variation doubles the ability of the cage 1.13' of this variation to increase the distraction of the interbody space, as a deployment of a second rotational element is also actuated in respect of the inferior surface 3.13*b* of the body 21.3 relative to the inferior vertebra 4*b*.

In variations of the invention, the fixed rods 27*a*, 27*a*', 27*b*, 27*b*' and the tip 28 of the bodies 2.11, 2.12, 12.13 and 12.13' of the twelfth and thirteenth embodiments may have different cross-sections, such as rectangular, oval, oblong, half-moon or race-track shaped.

According to FIGS. 46 to 50*b*, the cage 1.14 of the fourteenth embodiment comprises a body 2.14 with a rotational element 12.14, which does not extend into the wedged-shaped anterior part 5.14 of the body 2.14 but is arranged with a partly circular anterior portion 33 at the anterior inner-side 10.14*a* of the cavity 9.14 of the body 2.14 and is prolonged by two opposing arcs 20.14*a*, 20.14*b* arranged mostly within the cavity 9.14 and spanning until the posterior part 6.14 of the cage 1.14.

Figure 47A:
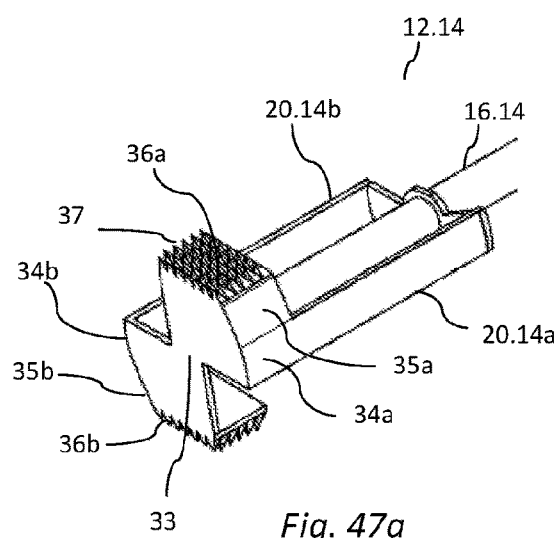
FIG. 47a represents a perspective view of the rotational element of the symmetric cage of the fourteenth embodiment.
Figure 47B:
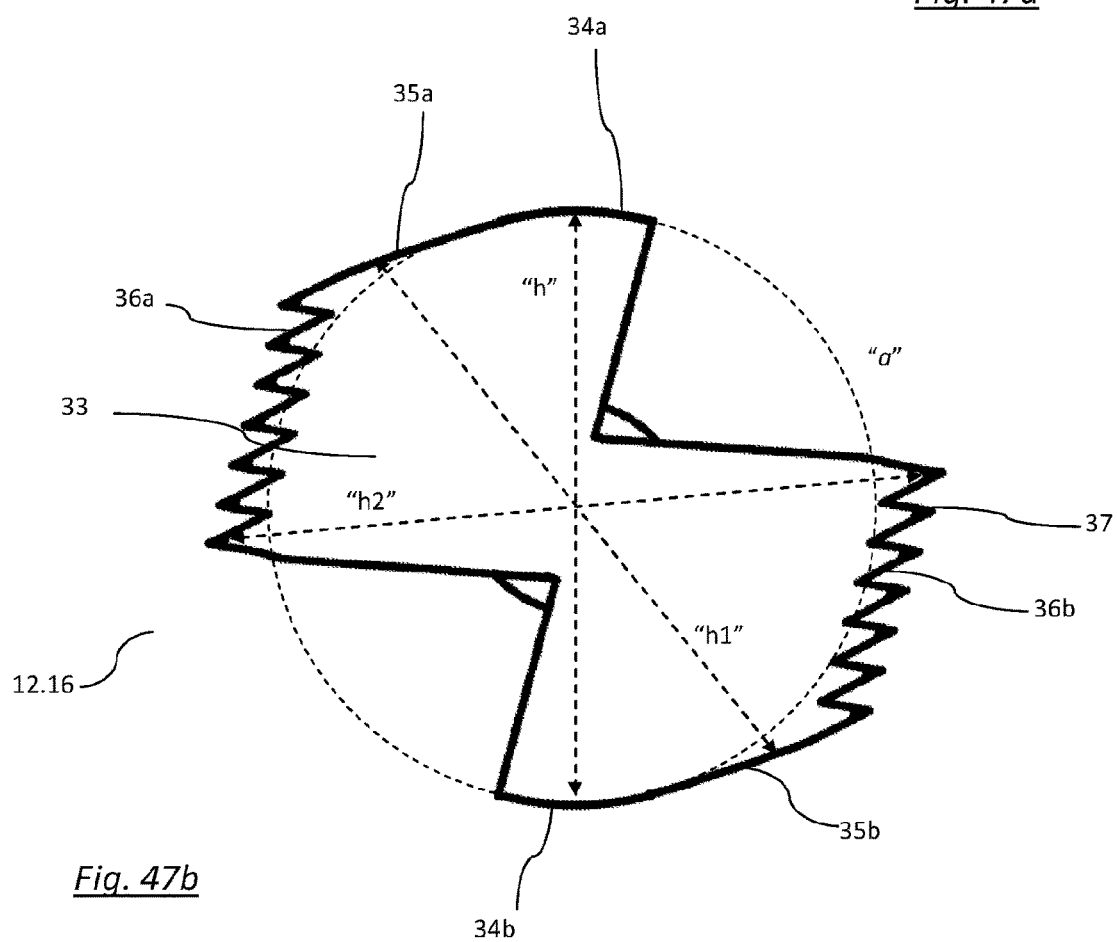

According to FIGS. 47*a* and 47*b*, the partially circular anterior portion 33, has two sets of three opposing surfaces 34*a*, 34*b*, 35*a*, 35*b*, 36*a*, 36*b* which have different shapes and profiles. The two opposing convex surfaces 34*a* and 34*b* are the prolongation of the arcs 20.14*a* and 20.14*b* and according to FIG. 47*b*, they define a height "h" and when rotated, an arc of circle "a". The center of the arc of circle "a" corresponds to the longitudinal medial axis of rotational element 12.14. As also described in FIG. 47*b*, the two opposing ellipsoidal surfaces 35*a* and 35*b* are separated by a distance "h1", which is superior to height "h". The two opposing surfaces 36*a*, 36*b* are essentially flat and also arranged in parallel to each other and are covered with crenellations 37. The distance "h2" between the peaks of the crenellations 37 on the flat surfaces 36*a* and 36*b* is superior to the distance "h1". When the rotational element 12.14 is laterally rotated of 90° or more, the increasing distances "h", "h1" and "h2" between the opposing respective surfaces 34*a*, 34*b*, 35*a*, 35*b*, 36*a*, 36*b*, gradually generate the desired distraction of the vertebrae 4*a*, 4*b* as they successively engage one set of surfaces after the next.

Figure 48A:
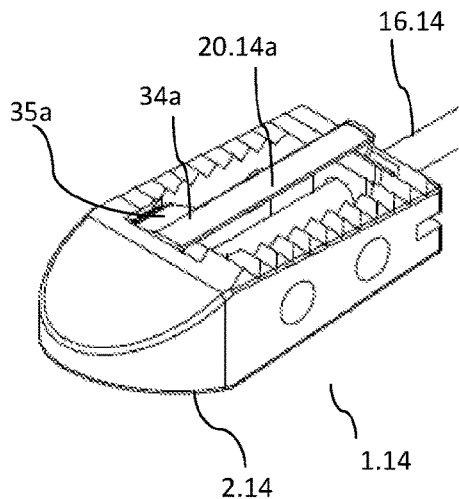
FIG. 48a represents a perspective view of the cage of the fourteenth embodiment in a first configuration prior to rotation of the rotational element.
Figure 48B:
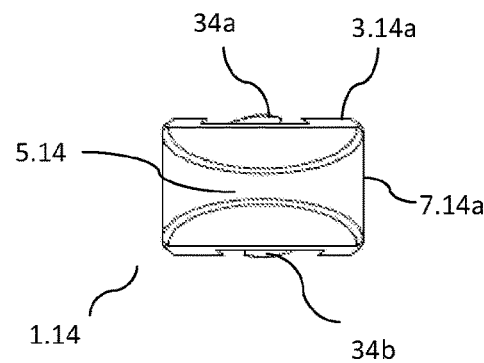
Figure 49A:
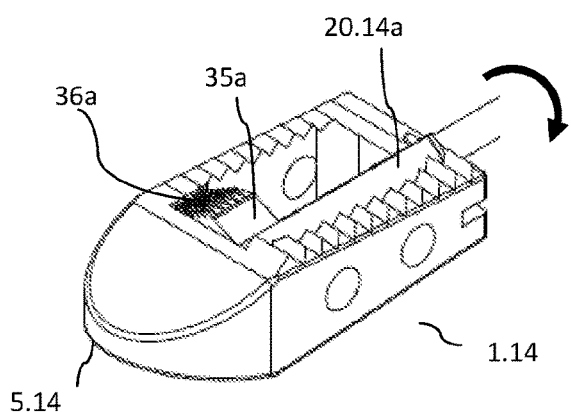
FIG. 49a represents a perspective view of the same cage as in FIGS. 48a and 48b but in a second configuration after 45° rotation of the rotational element.
Figure 49B:
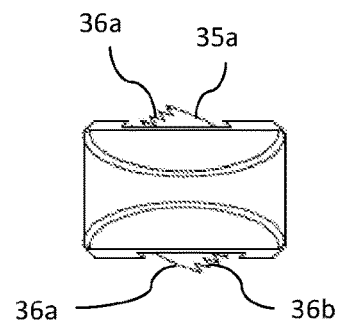
Figure 50A:
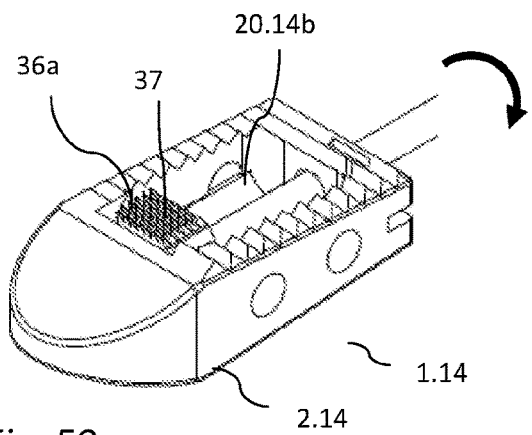
FIG. 50a represents a perspective view of the same cage as in FIGS. 48a and 49a but in a third configuration after 90° rotation and full deployment of the rotational element.
Figure 50B:
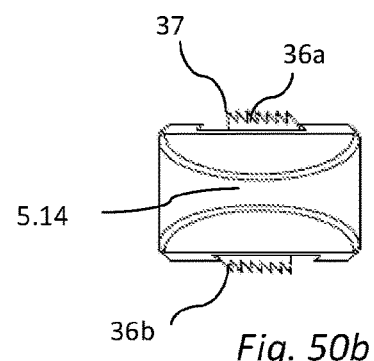
Figure 51:
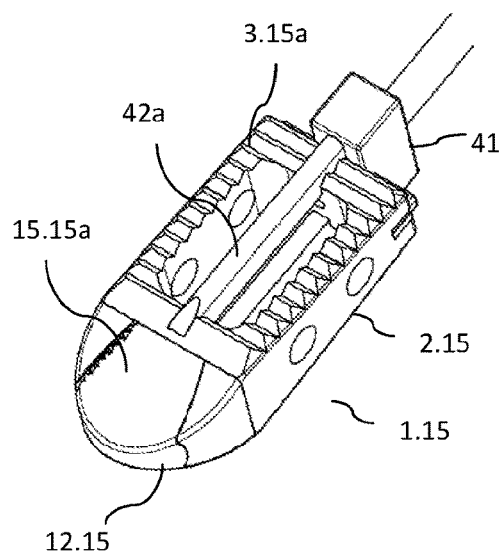
FIG. 51 represents a perspective view of the cage of the fifteenth embodiment fully assembled with shielding rods of a delivery system.
Figure 52:
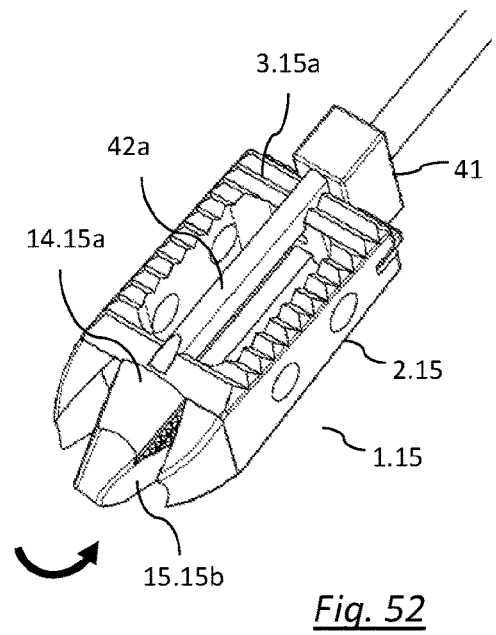
FIG. 52 represents a perspective view of the same cage as in FIG. 51 in a second configuration after partial deployment of the rotational element.

FIGS. 48*a* to 50*b* describe the cage 1.14 with the rotational element 12.14 in three different configurations. FIGS. 48*a* and 48*b* describe the rotational element 12.14 in a first configuration when the cage 1.14 is being inserted between two adjoining vertebrae 4*a*, 4*b*. In this first position, the convex opposing surfaces 34*a*, 35*b* of the rotational element typically engage the vertebrae 4*a*, 4*b*, as already described with the arcs 20.8*a*, 20.8*b* of the ninth embodiment; the vertebrae are now separated by the height "h". The arcs 20.14*a*, 20.14*b* shield the endplates of the vertebrae 4*a*, 4*b* against the crenellated superior and inferior surfaces 3.14*a*, 3.14*b* of the body 2.14. FIGS. 49*a* and 49*b* describe the cage 1.14 when it is in its final position in the interbody space during the rotation process of the rotational element 1.14, said rotational element having been rotated approximately 45°: the arcs 20.14*a*, 20.14*b* are collapsing sideways against the lateral inner-sides 9.14*a*, 9.14*b* of the cavity 9.14 of the body 2.14. The ellipsoidal opposing surfaces 35*a*, 35*b* of the partially circular anterior portion 33 of the rotational element 12.14 have emerged from the slit 22.14*a*, 22.14*b* and may now engage the vertebrae 4*a*, 4*b*, generating the expansion of the interbody space up to height "h1". FIGS. 50*a* and 50*b* describe the cage 1.14 with a fully expanded rotational element 12.14 in a final configuration after another lateral rotation of the mobile rod 16.14 of approximately 45°: the crenellations 37 on the flat opposing surfaces 36*a*, 36*b* may fully engage the vertebrae 4*a*, 4*b* expanding the interbody space to the height "h2". The full lateral rotation exercised between the first configuration in FIG. 48*a* and the final configuration in FIG. 50*a* is approximately 90°. The result of the expansion of the rotational element 12.14 from a first configuration to a last configuration is to increase the height of the anterior portion of the cage 1.14 and thus the angle relative to the posterior part 6.14 of the cage 1.14 which has not been heightened in the process moving from height "h" to height "h2".

In a variation of the fourteenth embodiment, the rotational element 12.14 can be arranged to define two heights "h" and "h1" or to define more than three heights or the gradients of a spiral. In other variations, rotational element 12.14 may be arranged with no opposing arcs and thus may consist only of its partly circular anterior portion 33. That partly circular portion may, in another variation, be arranged with an oval or race-track-shaped cross-section.

In another variation of the fourteenth embodiment, the ellipsoidal characteristics of the rotational element 12.14 may be applied to a rotational element to be arranged within the open receiving cavity 11.14 in the wedge-shaped anterior part 5.14' of the body 2.14': Such variation could for example take the shape of a wedge-shaped rotational element 12.14 similar to the crenellated wedge-shaped rotational elements 12.1' and 12.1" of the second embodiment shown in FIGS. 7*d*, 31*a* and 31*c*, the lateral sides 14.14*b*, 14.14*b* of which would be arranged with a first smooth section defining height "h" for the insertion of the cage 1.14' of this variation, and a second section covered with crenellations 40, defining a higher height "h2" of the rotational element 12.14 for the final anchoring of the cage 1.14' into the vertebrae 4*a*, 4*b*. The two sections of the lateral sides 14.14*a*, 14.14*b* may also be arranged with two smooth surfaces of different heights "h", "h2". Given the two different planes defined by the two respective sections of the lateral sides 14.14*a*, 14.14*b* of the rotational element, similar to planes P and P''' of the cage 1.1" of the second embodiment shown in FIG. 31*b*, the full deployment of such a wedge-shaped rotational element 12.14' of this variation is achieved after a rotation exceeding 90°, such as 110°. In a further variation of that variation of the fourteenth embodiment, the lateral sides 14.14*a*, 14.14*b* of the wedged-shape rotational element 12.14' may be arranged in two respective axes converging towards the posterior side 13.14*b*' of the rotational element 12.14' to create a gradient consistent with that of the superior and inferior surfaces 3.14*a*', 3.14*b*' of the body 2.14' of the cage 1.14'.

Figure 53:
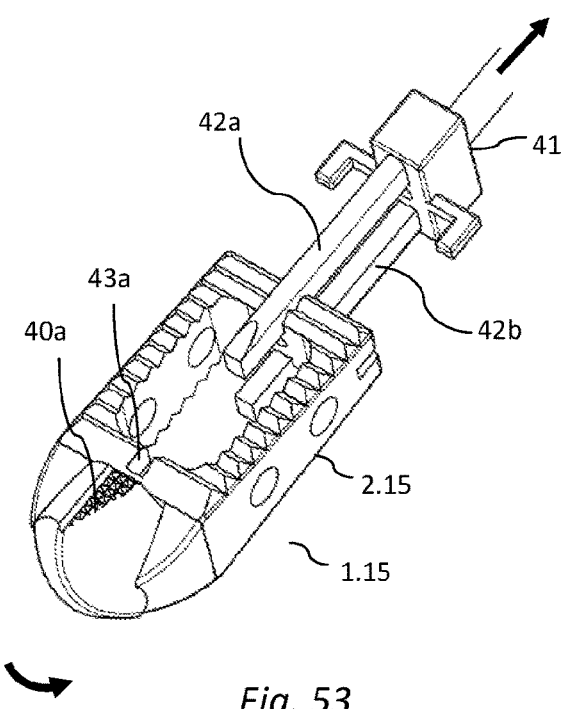
FIG. 53 represents a perspective view of the same cage as in FIGS. 51 and 52, in a third configuration after an additional 20°-40° rotation of the rotational element and partial disengagement of the shielding rods.
Figure 54:
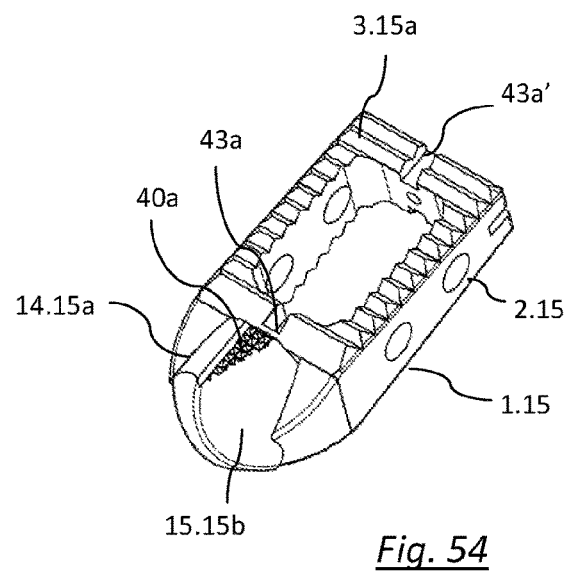
FIG. 54 represents a perspective view of the same cage as in FIGS. 51 to 53, in a final configuration after removal of the delivery system.

In a fifteenth embodiment of the invention described in FIGS. 51 to 54, the cage 1.15 may comprise a rotational element 12.15 and a body 2.15 similar to those of the second embodiment, the body 2.15 being arranged with one or more elongated receiving grooves 43*a*, 43*a*', 43*b*, 43*b*' carved in the superior and/or inferior surfaces 3.15*a*, 3.15*b* of the body 2.15 in the longitudinal axis of said body. The grooves 43*a*, 43a', 43b, 43b' are arranged to receive one or more shielding rods 42a, 42b connected to a delivery system 41 for the cage 1.15. These shielding rods 42a, 42b shield the vertebrae against the abrasion of the crenellations on the superior and inferior surfaces 3.15a, 3.15b of the body when the cage 1.15 is introduced into the interbody space in the same manner as the arcs of the seventh embodiment do. After the rotational element 12.15 is rotated back or maintained deployed (as shown in FIG. 53), the shielding rods 42a, 42b are pulled back from the grooves 43a, 43a', 43b, 43b' when the delivery system 41 is pulled out of the interbody space.

The cage 1.15 of this fifteenth embodiment may combine a rotational element 12.15 and a body 2.15 of any of the other embodiments, as long as the body 12.15 is arranged with at least one groove or one set of grooves 43a, 43a', 43b, 43b' on the superior or inferior surfaces 3.15a, 3.15b, or on both those surfaces, of the body 2.15.

The fifteen embodiments of the invention may combine some characteristics of the body 2 of one of the embodiments, with some characteristics of the rotational elements 12 of other embodiments, and some portions of the rotational element 12 or the body 2 may have the characteristic of one embodiment, while other portions of the rotational element 12 or the body may have the characteristic of another embodiment.

Each of the cages of the first to fifteenth embodiments of the invention and their variations may be arranged with a rotational element that only engages one vertebra at a given time during the insertion of the cage.

The bodies 2 of the cages 1 of the first to fifteen embodiments and the rotational elements 12 may be made in different materials: for instance, the rotational element 12 may be in rigid material (whether or not promoting adhesion to bone), to durably define the height of the intervertebral space while the bodies 2 may be in softer material to reduce the shield effect of the body 2 against the vertebrae 4a, 4b, or vice versa.

The rotation of the expansion element 12 is described as actuated through the means of a mobile rod 16, but may in different variations be achieved through any other technical means not requiring a rod 16.

All embodiments of the invention and methods of insertion may be applicable to interbody cages which are not made in one single block, such as expandable cages wherein two essentially flat-surfaced components, reflecting the features of the superior and inferior surfaces of the cages of the fifteen embodiments of the invention, are arranged to engage the vertebrae, such essentially flat-surfaced components being mobile relative to each other and are connected anywhere between their posterior and anterior parts through a hinge or other connecting means.

The invention claimed is:

1. An implantable device having a top and bottom surfaces with proximal and distal ends comprising:
   a stowable cambered element being a cover at the top of the implantable device forming a convex shield structure thereof;
   the bottom surface being substantially planar adapted to rest against an inferior vertebra;
   a shaft coupled to the stowable cambered element extending from the proximal end to the distal end of the implantable device;
   a tapered element forming the distal end of the implantable device;
   wherein the tapered element enables insertion of the implantable device by increasing a separation space between the upper and lower vertebra, and the stowable cambered element further increases the separation space to position the device at the implant site.

2. The implantable device of claim 1 wherein the stowable cambered element is stowed inside the device.

3. The implantable device of claim 1 wherein the stowable cambered element is stowed outside the device.

4. The implantable device of claim 1 wherein the stowable cambered element includes a strip spanning across the proximal and distal ends and shielding a portion of the top of the implantable device.

5. The implantable device of claim 1 wherein the stowable cambered element increases the form factor of the implantable device to advance and position the device between the separation space of the vertebrae.

6. The implantable device of claim 1 wherein the stowable cambered element is independently operable to rotate around the shaft to dynamically change from a first stowed position to a deployed second position forming a separation barrier between the upper vertebra and the top of the implantable device.

7. The implantable device of claim 1 wherein the top of the device includes crenellated edges to enable a secure fixation of the implantable device in the separation space between the upper and lower vertebra.

8. The implantable device of claim 1 wherein the top of the device includes crenellated edges with arcuate gradient to enable a secure fixation of the implantable device in the separation space between the upper and lower vertebra.

9. A method of implanting an intervertebral implantable device comprising the steps of:
   separating an upper and lower vertebra to advance the device in an interstitial space between an upper and lower vertebra to an implant site;
   actuating a cambered element or convex shield to dynamically change from a first stowed position to a second deployed position to cover a top section of the implantable device thereby increasing the form factor of the implantable device;
   advancing the implantable device in the interstitial space between the upper and lower vertebra with the cambered element forming a cover thereon to thereby deliver the implantable device at the implant site;
   retracting the cambered element from the deployed position to a stowed position; and
   exposing crenellated surfaces to secure the implantable device at the implant site.

10. The method of claim 9 wherein the step of separating the upper and lower vertebra includes introducing a tapered element in the interstitial space between the vertebrae increasing the space therebetween.

11. The method of claim 9 wherein the step of retracting the cambered element includes reducing the form factor of the implantable device.

12. The method of claim 9 wherein said step of actuating the cambered element from a stowed to a deployed position and advancing the implantable device in position include a further step of protecting the upper vertebra from exposure to the crenellated surfaces.

13. The method of claim 9 wherein said step of actuating includes rotating the cambered element from outside the implantable device.

14. The method of claim 9 wherein said steps of actuating includes rotating the cambered element on its own axis, independent of the implantable device, from a stowed position to a deployed position on top of the implantable device.

15. The method of claim 9 wherein said steps of retracting includes rotating the cambered element on its own axis, independent of the implantable device, from a deployed position to a stowed position within or outside the implantable device.

16. An implantable device having a top and bottom surfaces with proximal and distal ends comprising:
   a stowable cambered element being rotatably mobile to cover the top of the implantable device forming a convex shield structure thereof;
   the bottom surface being substantially planar adapted to rest against an inferior vertebra;
   a shaft, rotatably coupled to the stowable cambered element around an axis independent of the implantable device, extending from the proximal end to the distal end of the implantable device;
   a tapered element forming the distal end of the implantable device; and
   wherein the tapered element enables insertion of the implantable device by increasing a separation space between the upper and lower vertebra, and the stowable cambered element further increases the separation space to position the device at the implant site.

17. The implantable device of claim 16 wherein the stowable cambered element is stowed within the implantable device.

18. The implantable device of claim 16 wherein the stowable cambered element is stowed outside the implantable device.

19. The implantable device of claim 16 wherein the stowable cambered element is independently operable to rotate around the shaft to dynamically change from a first stowed position inside or outside the implantable device to a deployed second position forming one of a top cover and a separation barrier between the upper vertebra and the implantable device.

* * * * *